(12) United States Patent
Larsen et al.

(10) Patent No.: US 10,155,090 B2
(45) Date of Patent: Dec. 18, 2018

(54) SYSTEM FOR DETERMINING POSITION OF AN ELEMENT IN RELATION TO ANOTHER ELEMENT USING MAGNETIC FIELDS

(71) Applicant: Novo Nordisk A/S, Bagsvaerd (DK)

(72) Inventors: Andre Larsen, Dragor (DK); Henrik Riehm Soerensen, Silkeborg (DK); Laurits Hoejgaard Olesen, Copenhagen K (DK); Nikolaj Frogner Krusell, Copenhagen OE (DK); Jens Christian Andersen, Roskilde (DK)

(73) Assignee: Novo Nordisk A/S, Bagsvaerd (DK)

( * ) Notice: Subject to any disclaimer, the term of this patent is extended or adjusted under 35 U.S.C. 154(b) by 741 days.

(21) Appl. No.: 14/349,033

(22) PCT Filed: Oct. 5, 2012

(86) PCT No.: PCT/EP2012/069729
§ 371 (c)(1),
(2) Date: Apr. 1, 2014

(87) PCT Pub. No.: WO2013/050535
PCT Pub. Date: Apr. 11, 2013

(65) Prior Publication Data
US 2014/0243750 A1 Aug. 28, 2014

Related U.S. Application Data

(60) Provisional application No. 61/545,693, filed on Oct. 11, 2011.

(30) Foreign Application Priority Data

Oct. 7, 2011 (EP) ..................................... 11184280

(51) Int. Cl.
*G01B 7/30* (2006.01)
*A61M 5/315* (2006.01)
(Continued)

(52) U.S. Cl.
CPC ...... *A61M 5/31568* (2013.01); *A61M 5/1452* (2013.01); *A61M 5/24* (2013.01);
(Continued)

(58) Field of Classification Search
CPC .. A61M 2005/3126; A61M 2205/3317; A61M 2205/3389; A61M 2205/6054;
(Continued)

(56) References Cited

U.S. PATENT DOCUMENTS 4,914,389 A * 4/1990 Juds ....................... G01D 5/145
180/400
5,134,369 A 7/1992 Lo et al.
(Continued)

FOREIGN PATENT DOCUMENTS

CN 101352592 A 1/2009
DE 4415668 A1 11/1995
(Continued)

OTHER PUBLICATIONS

DuPont Displays, LCD technology fact sheet, 2009.
(Continued)

*Primary Examiner* — Jay Patidar
(74) *Attorney, Agent, or Firm* — Wesley Nicolas

(57) ABSTRACT

System comprising a sensor assembly (3, 4, 5, 6) adapted to measure a magnetic field, and a moveable element (1) adapted to be moved relative to the sensor assembly between two positions by a combined axial and rotational movement, the rotational movement having a pre-determined relationship to the axial movement. A magnet (3) is mounted to the moveable element and configured to generate a spatial magnetic field which relative to the sensor assembly varies corresponding to both the axial and rotational movement of the magnet and thus the moveable element. A processor is
(Continued)

configured to determine on the basis of measured values for the magnetic field an axial position of the moveable element.

11 Claims, 14 Drawing Sheets

(51) Int. Cl.
    *A61M 5/145* (2006.01)
    *A61M 5/24* (2006.01)
    *G01D 5/14* (2006.01)
    *G01R 33/02* (2006.01)
    *G01D 18/00* (2006.01)
    *A61M 5/31* (2006.01)

(52) U.S. Cl.
    CPC .... *A61M 5/31525* (2013.01); *A61M 5/31533* (2013.01); *G01B 7/30* (2013.01); *G01D 5/145* (2013.01); *G01D 18/004* (2013.01); *G01D 18/008* (2013.01); *G01R 33/0206* (2013.01); *A61M 2005/3126* (2013.01); *A61M 2205/3317* (2013.01); *A61M 2205/3389* (2013.01); *A61M 2205/6054* (2013.01); *A61M 2209/086* (2013.01)

(58) Field of Classification Search
    CPC .......... A61M 2209/086; A61M 5/1452; A61M 5/24; A61M 5/31525; A61M 5/31533; A61M 5/31568; G01B 7/30; G01D 18/004; G01D 18/008
    USPC .......................................... 324/207.2–207.25
    See application file for complete search history.

(56) References Cited

U.S. PATENT DOCUMENTS

| | | | |
|---|---|---|---|
| 5,400,195 A | 3/1995 | Morii et al. | |
| 5,569,212 A | 10/1996 | Brown | |
| 5,602,681 A * | 2/1997 | Nakayama | G01D 5/145 324/207.21 |
| 5,782,814 A | 7/1998 | Brown et al. | |
| 5,859,531 A | 1/1999 | Maurice et al. | |
| 5,879,297 A | 3/1999 | Haynor et al. | |
| 5,955,881 A * | 9/1999 | White | G01B 7/02 324/207.2 |
| 6,057,682 A | 5/2000 | McCurley et al. | |
| 6,400,142 B1 * | 6/2002 | Schroeder | B62D 15/02 324/207.21 |
| 6,411,082 B2 * | 6/2002 | Glasson | G01D 5/04 324/207.2 |
| 6,482,185 B1 | 11/2002 | Hartmann | |
| 6,496,003 B1 * | 12/2002 | Okumura | G01D 5/145 180/400 |
| 6,556,005 B1 | 4/2003 | Oomkes | |
| 6,563,306 B2 * | 5/2003 | Sato | G01B 7/003 324/207.2 |
| 6,940,275 B2 * | 9/2005 | Sogge | G01D 5/145 324/207.2 |
| 7,008,399 B2 | 3/2006 | Larsen et al. | |
| 7,049,808 B2 | 5/2006 | Martinez et al. | |
| 7,138,806 B2 | 11/2006 | Gafner et al. | |
| 7,242,182 B2 | 7/2007 | Finkler et al. | |
| 7,589,522 B2 * | 9/2009 | Knecht | G01D 5/145 324/207.16 |
| 7,936,437 B2 | 5/2011 | Hong et al. | |
| 8,203,331 B2 * | 6/2012 | Erickson | G01D 5/145 324/207.13 |
| 8,283,914 B2 | 10/2012 | Mehnert et al. | |
| 2006/0161112 A1 | 7/2006 | Steffen | |
| 2006/0175427 A1 | 8/2006 | Jonientz et al. | |
| 2007/0066940 A1 | 3/2007 | Karunaratne et al. | |
| 2007/0167703 A1 | 7/2007 | Sherman et al. | |
| 2008/0079423 A1 * | 4/2008 | Wolf | G01D 5/145 324/207.25 |
| 2008/0169307 A1 | 7/2008 | Hofstetter | |
| 2009/0318865 A1 | 12/2009 | Moller et al. | |
| 2010/0163333 A1 * | 7/2010 | Patil | B62D 15/0215 180/402 |
| 2011/0175601 A1 * | 7/2011 | Bogos | G01D 5/14 324/207.25 |
| 2012/0161755 A1 | 6/2012 | Masson et al. | |
| 2013/0194185 A1 | 8/2013 | McLoughlin et al. | |
| 2015/0160042 A1 * | 6/2015 | Bogos | G01D 5/145 324/207.15 |
| 2016/0051760 A1 | 2/2016 | Krusell et al. | |
| 2016/0051764 A1 | 2/2016 | Dreier et al. | |

FOREIGN PATENT DOCUMENTS

| | | |
|---|---|---|
| DE | 102008024103 A1 | 11/2008 |
| DE | 102007036984 A1 | 1/2009 |
| EP | 1911479 A1 | 4/2008 |
| EP | 2354769 A1 | 8/2011 |
| EP | 2359884 A2 | 8/2011 |
| JP | 2012187203 A | 10/2012 |
| WO | 9714933 A2 | 4/1997 |
| WO | 9961868 A1 | 12/1999 |
| WO | 00/32088 A1 | 6/2000 |
| WO | 0167412 A2 | 9/2001 |
| WO | 02064196 | 8/2002 |
| WO | 03005891 A1 | 1/2003 |
| WO | 03020545 A1 | 3/2003 |
| WO | 2004009720 A2 | 1/2004 |
| WO | 2004070321 A1 | 8/2004 |
| WO | 2007107564 A1 | 9/2007 |
| WO | 2009/024562 A1 | 2/2009 |
| WO | 2010/037828 A1 | 4/2010 |
| WO | 2010/052275 A2 | 5/2010 |
| WO | 2010/098927 A1 | 9/2010 |
| WO | 2010112575 A1 | 10/2010 |
| WO | 2011/117212 A1 | 9/2011 |
| WO | 2012019958 A2 | 2/2012 |
| WO | 12129247 A2 | 9/2012 |
| WO | 2013004844 A1 | 1/2013 |
| WO | 2013050535 A2 | 4/2013 |
| WO | 2014161954 A1 | 10/2014 |

OTHER PUBLICATIONS

Innovative Human—Systems Interface, Optical Bonding and Lamination Capabilities, http://www.ieeinc.com/sites/default/files/military/group/pdf/Optical %20Bonding%20Capabilities_0.pdf.

Samsung Electronics, Flexible LCD Panel features 7 in. diagonal screen, Nov. 28, 2005, South Korea, http://news.thomasnet.com/fullstory/Flexible-LCD-Panel-features-7-in-diagonal-screen-470952, retrieved on Dec. 13, 2013.

Joon Kim, Bestech Corp,Flexible Displays in AMOLED Technology, Jul. 3, 2013, http://monitorsolution.blogspot.in/2013/07/fiexible-displays-in-amoled-technology.html, retrieved on Aug. 4, 2015.

DuPont Displays, Putting Science to work for displays, 2009.

Flexible LCDs: http://www.pocket-lint.com/news/123710-e-ink-talks-kindle-displays-and-a-flexible-approach-to-smartwatches http://www.alibaba.com/showroom/flexible-lcd-display.html http://dx.com/p/flexible-1-0-lcd-mp3-player-with-usb-tf-sd-slot-and-remote-controller-black-42566. Accessed on Sep. 3, 2015.

* cited by examiner

Fig. 16A
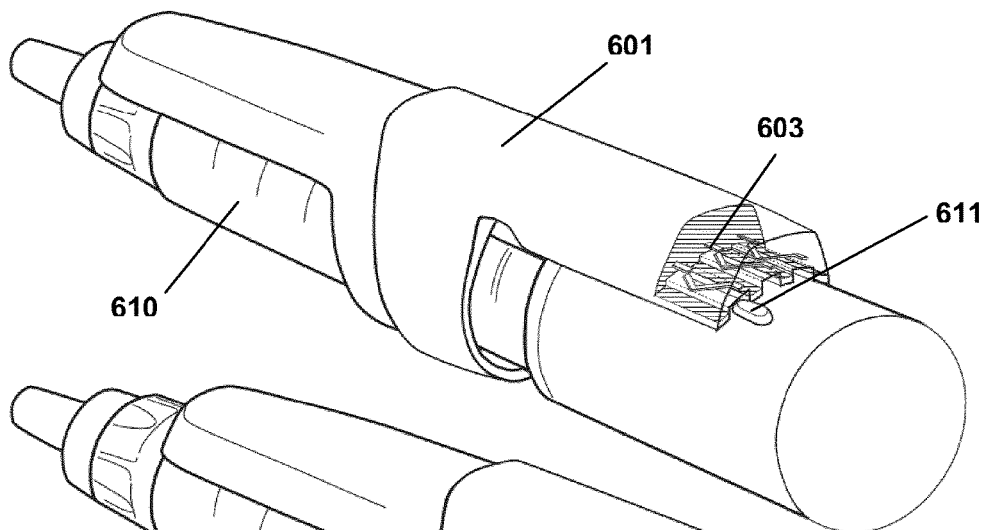
Fig. 16B
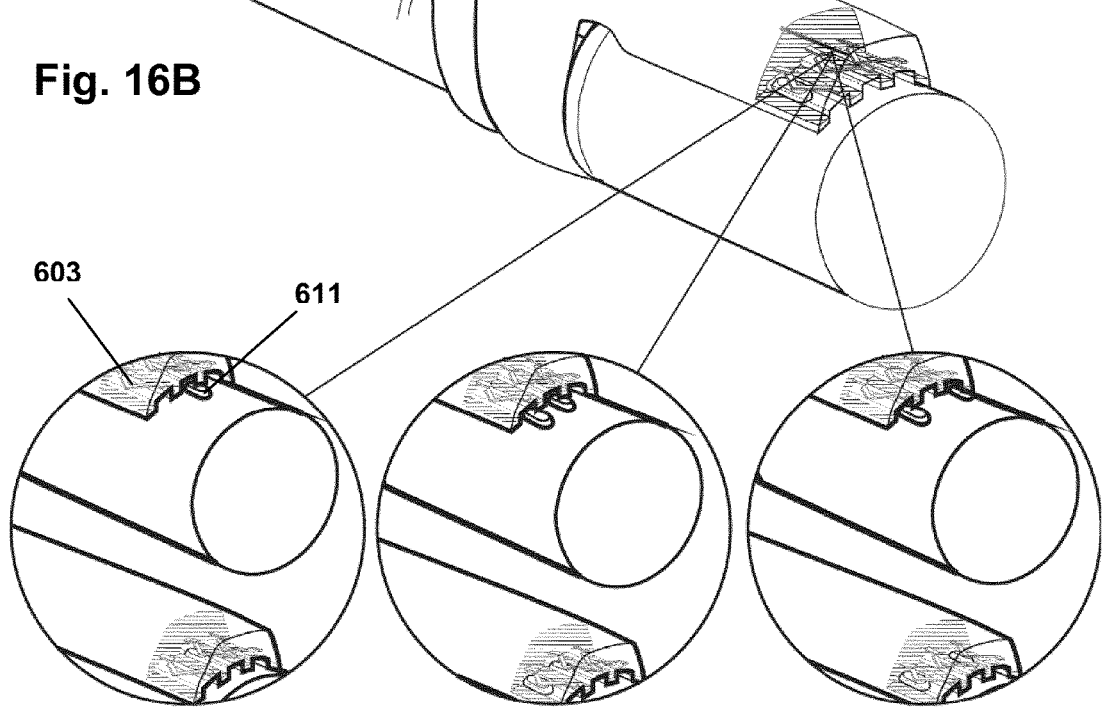
Fig. 16C          Fig. 16D          Fig. 16E

SYSTEM FOR DETERMINING POSITION OF AN ELEMENT IN RELATION TO ANOTHER ELEMENT USING MAGNETIC FIELDS

CROSS-REFERENCE TO RELATED APPLICATIONS

This application is a 35 U.S.C. § 371 National Stage application of International Application PCT/EP2012/069729 (published as WO 2013/050535), filed Oct. 5, 2012, which claimed priority of European Patent Application 11184280.3, filed Oct. 7, 2011; this application claims priority under 35 U.S.C. § 119 of U.S. Provisional Application 61/545,693; filed Oct. 11, 2011.

The present invention relates to systems and methods for detecting the position of a moveable element. The invention addresses the issue of determining the axial and/or rotational position of an element which is moved both axially and rotationally. In a specific aspect, the invention addresses the issue of determining the axial position of an element which is moved corresponding to a threaded relationship between the moveable element and a further element.

BACKGROUND OF THE INVENTION

In the disclosure of the present invention reference is mostly made to drug delivery devices comprising a threaded piston rod, such devices being used e.g. in the treatment of diabetes by delivery of insulin, however, this is only an exemplary use of the present invention.

Drug Injection devices have greatly improved the lives of patients who must self-administer drugs and biological agents. Drug Injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems.

Though some injection devices integrate this monitoring/acquisition mechanism into the device itself, e.g. as disclosed in US 2009/0318865 and WO 2010/052275, most devices of today are without it. The most widely used devices are purely mechanical devices either durable or prefilled. The latter devices are to be discarded after being emptied and so inexpensive that it is not cost-effective to build-in electronic data acquisition functionality in the device itself.

Whereas the above-referred known systems are based on detecting movements generated by the expelling mechanism which then represent translation of the actual expelling structure, i.e. the reservoir piston or the piston rod in direct contact with the piston, it has also been proposed to directly measure the position of the piston. For example, U.S. Pat. No. 5,782,814 discloses a system in which the piston includes a magnetically responsive element, such as an iron core. The system has a receptacle for receiving a syringe reservoir for dose measurement. An inductive element is positioned coaxially to the receptacle to produce a magnetic field. When the syringe is placed in the receptacle, the intensity of the magnetic field varies in dependence upon the position of the piston in the reservoir. The magnetic field induces a voltage in a conducting loop and a voltage meter is connected to the conducting loop to measure the induced voltage. A microprocessor is connected to the voltage meter to calculate the dose from the measurement of the induced voltage. U.S. Pat. No. 6,556,005 discloses a magnetic encoder apparatus capable of determining axial and rotational displacements.

Having regard to the above, it is an object of the present invention to provide systems and methods for reliable and efficient detection of the axial position of an axially moveable element. It is a further object of the invention to provide systems and methods allowing an expelled dose of drug from a drug delivery device to be determined. It is a yet further object to provide means allowing a log for determined values to be created in a safe and efficient way.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention a system is provided, comprising a sensor assembly comprising one or more sensors each adapted to measure a magnetic field corresponding to three axes, and a moveable element adapted to be moved relative to the sensor assembly by a combined axial and rotational movement corresponding to a pre-defined axis, the rotational movement having a pre-determined relationship to the axial movement, e.g. the moveable element is moved corresponding to a threaded relationship between the moveable element and a further element. A magnet is incorporated in the moveable element and moving together therewith, the magnet being configured to generate a spatial magnetic field which relative to the sensor assembly varies corresponding to both the axial and rotational movement of the magnet and thus the moveable element, thereby generating a spatial magnetic field which varies uniquely relative to each sensor. A processor is configured to determine on the basis of measured values for the magnetic field an axial position of the moveable element relative to a given position. The pre-determined relationship may be in the form of a threaded relationship between the moveable element and a further element.

The determined value may be communicated directly to a user, e.g. measured in mm, or used to calculate a dependent value, e.g. two measured values could be used to calculate an amount of drug expelled from a cartridge by a piston moved by a piston rod. In addition, with a defined zero-position the axial position of the moveable element can be communicated as amount of total expelled drug or remaining drug in the reservoir.

The term "magnet" indicates any configuration of magnetic means capable of creating a useful magnetic field. The magnet may thus be an active magnet or a passive magnet which produces a magnetic field only when influenced by external means. The magnet may be in the form of an assembly comprising more than one magnet. One or more magnets may be arranged to enhance position detection and potentially reduce the number of sensors, e.g. by providing a stronger magnetic field, placing magnets in suitable distance to sensors or provide a field signature which is more distinguishable from external fields. The magnet may be a permanent magnet mounted to the moved element or the moved element may comprise material which can be permanently magnetized to create a permanent magnet. The three axes of each sensor may be arranged perpendicularly relative to each other. The axial movement may be linear or curved, the latter being relevant e.g. for a curved and flexible piston rod.

The sensor assembly may comprise a number of sensors arranged to achieve the best optimum in respect of the number of sensors utilized and the required precision for the determined position. For example, the sensor assembly may be configured as one or more rings each consisting of 2 or more sensors placed equidistant around the pre-determined axis. Alternatively, the sensors of the sensor assembly may be arranged substantially along a line in parallel with the pre-determined axis along which the moveable element is moved.

In exemplary embodiments the processor is configured to calculate the difference between measured sensor values and expected sensor values, wherein determination of the axial position of the moveable element is based on the calculated difference between the expected sensor values and the measured sensor values. The expected sensor values can be derived using an analytical model of the field, e.g. a dipole field model of the magnet. If the sensor assembly places the sensors in the near-field of the magnet, the model can be based on a finite element analysis of the magnetic field accounting for the magnet structure. The invention also provides corresponding methods.

For example, the processor means may be adapted to, on the basis of field difference between measured and expected sensor values, determine the deviation of model fit and estimate which system parameters that causes the deviation. The transformation from field differences to model fit deviation could be accomplished by having a model (e.g. linearized) of the system based on derivatives of selected system parameters. This can be done by determining the derivatives of the model of the expected sensor values with respect to each of the system parameters that is included, e.g. offset of magnet angle relative to a pre-determined mechanical geometry. The invention also provides corresponding methods.

In an exemplary embodiment the system comprises memory means in which a nominal model of the system comprising a number of system parameters is stored, the processor means being configured to calculate for each sensor and each axis a difference between a measured sensor value and the expected nominal sensor value, transform the difference into deviations of selected system parameters, re-adjust the expected sensor values into (e.g. linearized) corrected sensor values based on the system parameter deviations, and determine an axial position of the moveable element being based on the calculated differences between the measured sensor values and the (linearized) corrected sensor values. The invention also provides a corresponding method.

Alternatively, expected sensor values can be based on measured sensor values, where the determination of the axial position of the moveable element is based on the calculated difference between sensor values.

In a further exemplary embodiment the processor means, on the basis of the measured values, is adapted to determine an initial axial position of the moveable element, determine a rotational position of the moveable element, and calculate a corrected axial position of the moveable element, wherein the calculation is based on the determined initial axial position, the determined rotational position, and the pre-determined relationship between the rotational and the axial movement.

The sensor assembly may be configured as one or more rings each consisting of two or more sensors placed around the pre-defined axis. The three axes of each sensor may be arranged perpendicularly relative to each other. The magnet may be a permanent magnet or an induced magnet.

In an exemplary embodiment the system comprises a drug delivery device comprising a reservoir or means for receiving a reservoir for a drug, the reservoir comprising an axially displaceable piston and an outlet, and a drug expelling mechanism for expelling drug from the reservoir and comprising the moveable element in the form of a threaded piston rod which during an expelling action performs the combined axial and rotational movement thereby axially moving the piston of a mounted reservoir. A display controlled by the processor means may be provided to display a calculated dose of drug to a user.

The system may comprise a measuring unit in which the sensor assembly and processor means are arranged, and which is configured to receive the drug delivery device in a pre-determined position, the measuring unit being configured to calculate the size of an expelled dose of drug based on two consecutive determinations of the axial position of the piston rod. The measuring unit may be in the form of a cap unit adapted to calculate the size of an expelled dose of drug when the cap unit is placed in its mounted position on the drug delivery device to cover the outlet of a mounted reservoir.

Alternatively the system may comprise a measuring assembly in which the sensor assembly and processor means are arranged, the measuring assembly comprising a measuring unit and a cap unit, wherein the measuring unit comprises the sensor assembly as well as coupling means allowing the measuring unit to be mounted on the drug delivery device with the sensor assembly in a pre-determined position relative to the piston rod, and wherein the cap unit is configured to be releasably mounted on the drug delivery device or the measuring unit to cover the outlet of a mounted reservoir.

In an exemplary embodiment of the system, the drug delivery device further comprises an identifier representing information for the specific drug type contained in the reservoir or the specific drug delivery device, and the measuring unit further comprises means for capturing information from the identifier, as well as logging means adapted to create a log for amounts of drug expelled from the reservoir based on calculated doses of drug, the log being created for a given identifier. The identifier may be a colour, in the form of a barcode, or in the form of a pattern of conductive elements. The sensor system may comprise a number of tables for different drug delivery devices, the identifier being used to select the appropriate table.

In further exemplary embodiments the processor means is adapted to, on the basis of model fit, determine system parameters identifying predefined characteristics of a drug delivery system, e.g. device type, drug type or drug concentration. For example, different magnetic signatures, e.g. magnet strength, could be used to identify different concentrations for a given drug, or the relation between rotational movement and axial movement could be used to identify dosing characteristics for the device, this indicating the type or concentration of drug contained in the device, e.g. whether insulin is provided with a concentration of 100 or 200 IU/ml. Examples of relations between rotational movement and axial movement are magnet starting angle and number of magnet revolutions for a given displacement.

In a further aspect of the invention a drug delivery system is provided comprising (a) at least one drug delivery device comprising a reservoir containing a drug, a drug expelling mechanism for expelling drug from the reservoir, and an identifier representing information for the specific drug type contained in the reservoir or the specific drug delivery device, as well as (b) a capture assembly releasably mountable on each of the drug delivery devices, comprising an electronically controlled capturing system for capturing data representing a property related to the amount of drug expelled from the reservoir by the expelling means, electronically controlled means for capturing information from the identifier, logging means adapted to create a log for amounts of drug expelled from the reservoir based on captured data, wherein the log is created for a given identifier.

The identifier may represent a given specific type of drug or a given unique drug delivery device. The identifier may be in the form of a colour marking, a barcode (e.g. 2D) or in the form of a pattern of conductive elements. The means for capturing information from the identifier may comprise a sensor adapted to capture information during movement of the sensor relative to the identifier.

In an exemplary embodiment the drug delivery device and the capture assembly comprises corresponding releasable mounting means adapted to mount the capture device in a pre-defined position relative to the drug delivery device, the mounting requiring a specified translational movement between the drug delivery device and the capture assembly, the translational movement allowing the sensor to capture information from the identifier.

Designing an electronic recording unit, that can automatically identify and recognise drug delivery devices with different contents will allow manufacturers a simpler and more cost efficient production and provide increased safety of the users.

Manufacturers will be able produce both drug delivery devices and electronic recording units in a more cost efficient way, since fewer distinguishing marks (and thus fewer parts) is needed to be able to distinguish between different contents and fewer different electronic recording units are necessary, the more devices with different contents each electronic recording unit is able to handle.

The safety of the users is increased since the electronic recording unit will reduce the risk of using a wrong product or dose by accident. Especially users using different products (contents) from similar devices are at risk of mistaking them for each other if devices appear to similar and may forget to set electronic recording unit to correct product if manual setting is required and electronic recording unit is applicable on different devices in use.

Furthermore automatic identification of device type and contents will allow for additional safety features to be incorporated in the electric recording unit, for instance warning the user if an unknown or counterfeit product is detected or if drug type or concentration is different than normally used.

In the context of the present application and as used in the specification and the claims, the term processor means covers any combination of electronic circuitry suitable for providing the specified functionality, e.g. processing and storing data as well as controlling all connected input and output devices. A processor will typically comprise one or more CPUs or microprocessors which may be supplemented by additional devices for support, storage or control functions. For example, in case a communication interface is provided (e.g. wireless), the transmitter and receiver may be fully or partly integrated with a processor, or may be provided by individual units. Each of the components making up the processor circuitry may be special purpose or general purpose devices. The term display means covers any type of display capable of visually providing the specified functionality, e.g. a LCD or OLED.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF THE DRAWINGS

In the following the invention will be further described with reference to the drawings, wherein FIGS. 16A-16E show a capture device comprising means for detecting an identifier, FIG. 17 show a further capture device comprising means for detecting an identifier.

DESCRIPTION OF EXEMPLARY EMBODIMENTS

Figure 1:
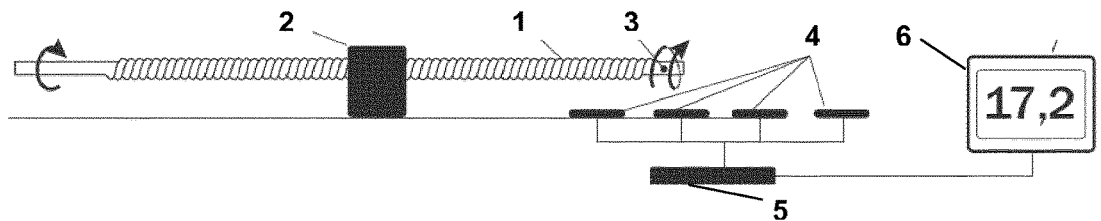
FIG. 1 shows a system for detecting the axial position of a threaded rod.

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only.

The magnetometer-based volume detection systems described in the following is basically systems that can accurately detect the position of a magnet moving along a predefined line. The systems are therefore applicable in many technical areas in which accurate non-contact position sensing is relevant. In the following systems will be described which have been set up for application in a drug delivery system comprising a threaded rod 1 guided in a correspondingly threaded housing 2 and thus configured to perform a linear motion along its axis when rotated, see FIG. 1. The distal end of the rod is provided with a magnet mounted with a polarity essentially perpendicular to the direction of linear movement. In the shown embodiment number of 3D magnetometers 4 are positioned along the line of movement for the rod. The measurements from the magnetometers are captured by a microprocessor system 5 connected to a display 6 adapted to show e.g. actual measurements from the magnetometers as well as display a value representing an axial position of the rod.

Figure 2A:
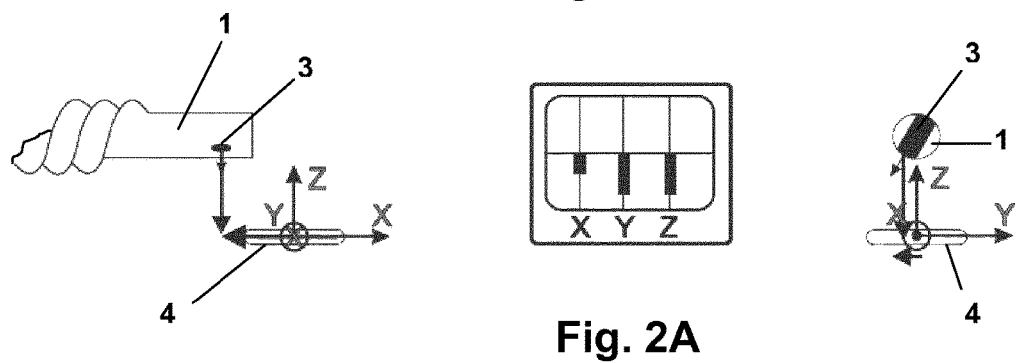
FIGS. 2A-2C show measured outputs from a 3D magnetometer.
Figure 2B:
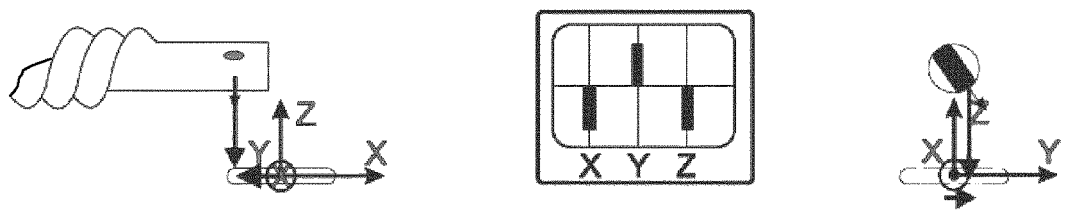
Figure 2C:
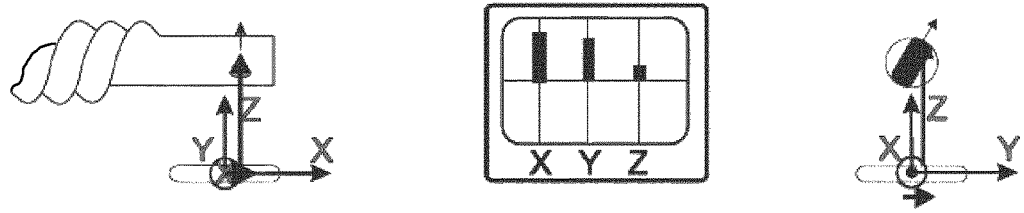

The 3D magnetometers 4 each measure the amplitude of the magnetic field in three perpendicular directions as illustrated in FIGS. 2A-2C for different rotational (and thus axial) positions of the rod 1. Since a fixed magnet 3 is used the amplitude of the magnetic field measured in each direction is determined by the distance between the magnet and the sensor.

The measured amplitude in three directions can be combined to a three dimensional vector, where the length of the vector represents the amplitude of the magnetic field and the direction of the vector represents the direction of the magnetic field relative to the sensor. It should be noted that the vector length does not represent the distance of the magnetic field from the sensor, since the amplitude increases when the distance decreases.

Figure 3A:
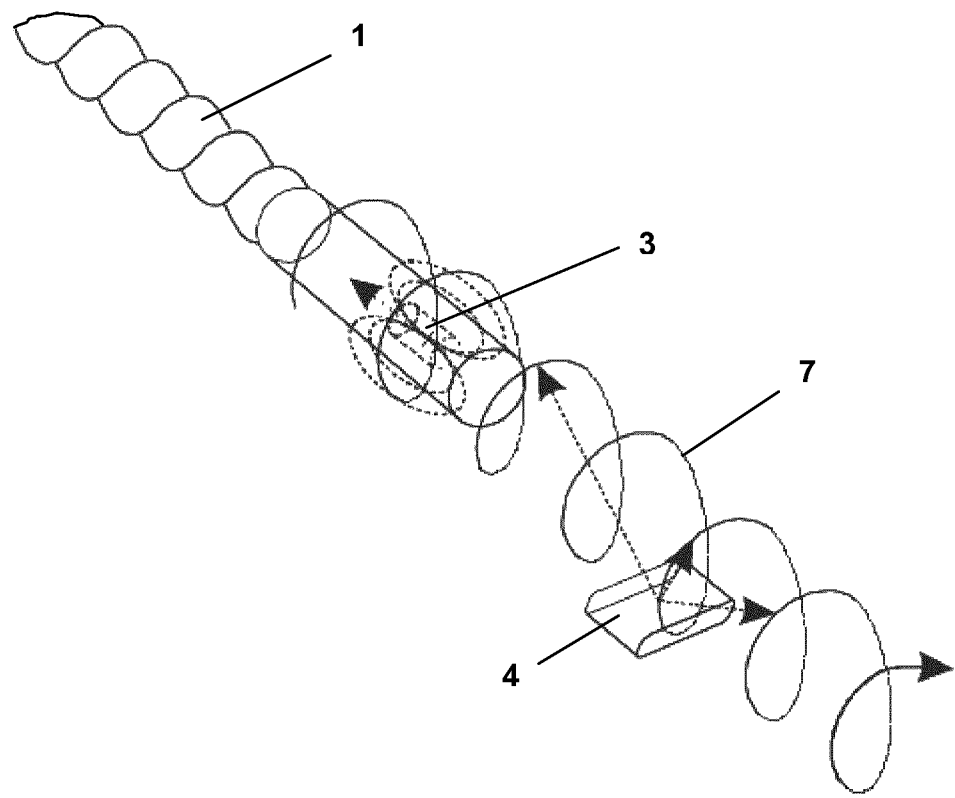
FIGS. 3A and 3B show variations in a magnetic field vector path.
Figure 3B:
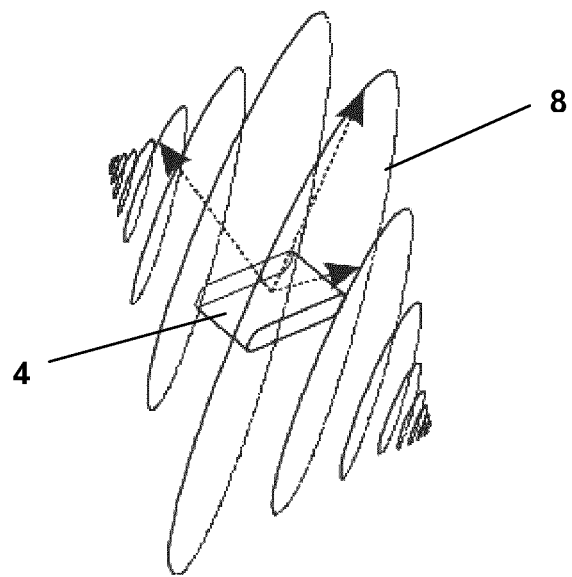

The screw-line motion 7 of the magnet will thus result in a 3-dimensional vector spiral 8 with increasing radius with the magnet moving closer to the position of minimum distance from the sensor, shifting to a decreasing radius when passing the point of minimum distance to the sensor, see FIGS. 3A and 3B showing the magnetic field vector path caused by rotation of the threaded rod.

Figure 4A:
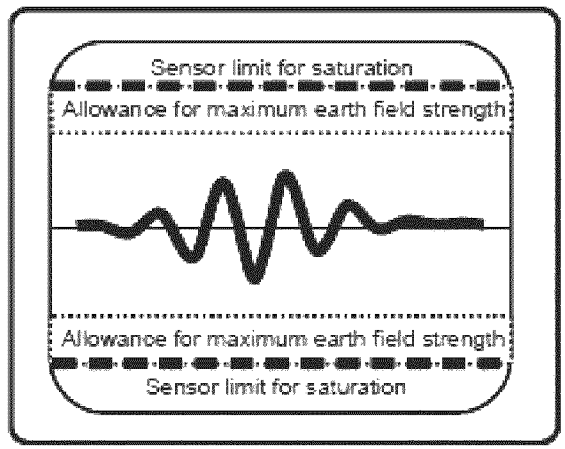
FIGS. 4A-4C show sensor measurements in relation to sensor saturation.
Figure 4B:
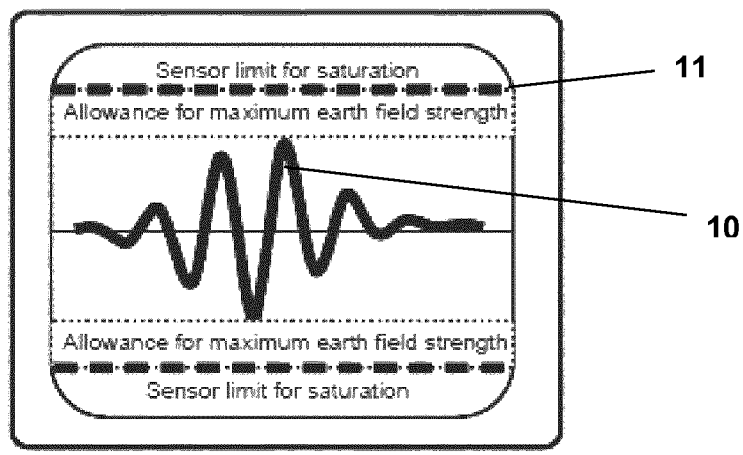
Figure 4C:
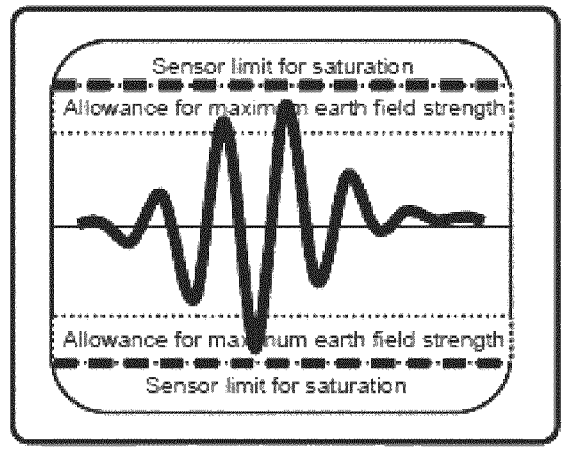

To optimize the signal-to-noise ratio, only the area of operation in which the amplitude of the magnetic field is significant, is used. When designing such a system, earth's magnetic field has to be taken into account. This is optimized by selecting a magnet with a field strength that in the position of minimum distance to the sensor results in an amplitude 10 that with the strongest possible earth field (it varies over the globe) only just allows for the sensor to measure without going in to a state of saturation 11, see FIGS. 4A-4C showing the results of using magnets with different strength. If the maximum amplitude of the magnetic field is not equally distributed on the three axes of the sensor, the sensors can be angled relative to the system in order to distribute the maximum field on the three sensor axes allowing a greater field strength of the selected magnet.

Figure 5:
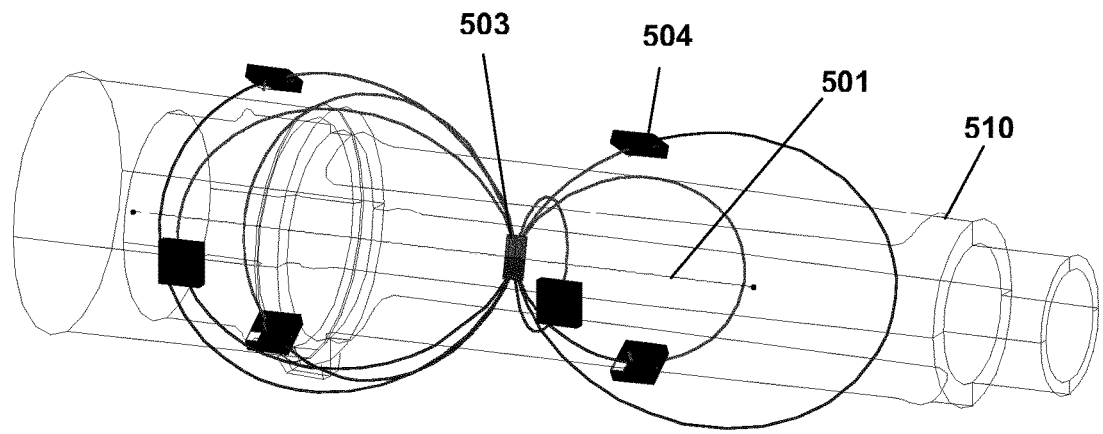
FIG. 5 shows a sensor assembly configured as two rings.

In FIG. 5 an exemplary embodiment of a sensor assembly is configured as two rings each consisting of 3 3D magnetic sensors 504 equidistantly around a pre-determined axis 501 for a rod element, the rod element being moved axially inside the distal portion 510 of a pen-formed drug delivery device corresponding to a threaded engagement with a stationary nut element and comprising a distally arranged permanent dipole magnet 503.

In the following an exemplary algorithm for estimating a current position and orientation of a magnet will be described. The algorithm is general to any movement of a magnet, but in the present application, it is applied to a system with a combined axial and rotation movement of a magnet. In order to state the axial displacement, the algorithm will have to determine the position of the magnet before and after movement.

The algorithm is adapted for a system having deviations from nominal movement of the magnet. Therefore, it requires a pre-determined model of the magnet movement from which one can derive derivatives. Let $B_{nom}^k(n)$ denote the field having nominal geometry of the system, where n is the position of the axial displacement and k is the sensor measuring the field.

If the magnet has a simple geometry and if the relative distance between sensors and magnet is assumed to be in the magnetic far-field for all positions, the pre-determined model can be estimated using a dipole field model. Thus, we can estimate $B_{nom}^k(n)$ to all positions by the following:

$$B_{nom}^k(n) = \frac{1}{4\pi}\left[\frac{3(m \cdot r)}{r^5} - \frac{m}{r^3}\right] \qquad [1]$$

Where m is the dipole moment vector of that given position n, r is the distance vector between the magnet and the sensor k and r is the distance between the magnet and sensor k.

If the sensors are positioned in the magnetic near-field, then $B_{nom}(n)$ can be estimated using Finite Element analysis of the magnet geometry.

The concept is to have a model that both estimates the non-nominal behaviour and compensates the pre-determined nominal model, if non-nominal behaviour is found to be acceptable. In order to do so, a linearized model of the pre-determined model is defined: [2]

$$\hat{B}_{k,n}(B^{ext}, \Delta x, \Delta y, \Delta z, \Delta m, \Delta \varphi, \Delta \psi) =$$

$$B_{nom}^k(n) + B^{ext} + \left[\frac{\partial B}{\partial x}\right]_{k,n}^{nom}\Delta x + \left[\frac{\partial B}{\partial y}\right]_{k,n}^{nom}\Delta y + \ldots + \left[\frac{\partial B}{\partial \psi}\right]_{k,n}^{nom}\Delta \psi$$

Where we have included the following Deviation parameters in the linearized model:
$B^{ext}$ Uniform background field
$\Delta x$, $\Delta y$ Radial offsets of magnet position relative to nominal model
$\Delta z$ Axial offset of magnet position relative to nominal model
$\Delta m$ Deviation from nominal magnet strength
$\Delta \varphi$ Rotational offset
$\Delta \psi$ Tilt offset Stacking the Deviation parameters in a column vector E:

$$E = \begin{bmatrix} \overline{B_x^{ext}} \\ \overline{B_y^{ext}} \\ B_z^{ext} \\ \Delta x \\ \Delta y \\ \Delta z \\ \Delta m \\ \Delta \varphi \\ \Delta \psi \end{bmatrix} \quad [3]$$

We can write a linearized model as:

$$\hat{b}_n(E) = b_n^{nom} + J_n E \quad [4]$$

Where $J_n = \partial b_n^{nom}/\partial E$ is the Jacobian matrix. Then we determine E to minimize the difference between the measured field and the linearized model. I.e.:

$$\frac{\partial \|b^{meas} - \hat{b}_n(E)\|}{\partial E} = 2 J_n^T G_n (b_n^{nom} + J_n E - b^{meas}) = 0 \quad [5]$$

Where $G_n$ denotes a diagonal matrix with weights for each sensor k and position n. Thus, E is given by:

$$E_n^{min} = [J_n^T G_n J_n]^{-1} [J_n^T G_n (b^{meas} - b_n^{nom})] \quad [6]$$

The above expression can be simplified to the following:

$$E_n^{min} = M_n (b^{meas} - b_n^{nom}) \quad [7]$$

Where:

$$M_n = [J_n^T G_n J_n]^{-1} [J_n^T G_n] \quad [8]$$

This matrix is constant. Thus, it can be stored on the processor to save computational power.

The parameter offset vector, $E_n^{min}$, is then inserted into the linearized model:

$$\hat{b}_n(E_n^{min}) = b_n^{nom} + J_n E_n^{min} \quad [9]$$

This provides an updated version of the nominal model accounting for the difference between the measured field and the nominal model. The estimated position is found to be the position with the smallest difference, i.e. minimizing the residual:

$$r^n = \|b^{meas} - \hat{b}_n(E_n^{min})\| \quad [10]$$

The advantages of the above algorithm are:

The algorithm makes use of constant tables that can be stored on the processor, i.e. it consists of $b_n^{nom}$, $J_n$ and $M_n$. The algorithm provides measures that can be used as fail-safe measure, i.e. the quality of the fit can be estimated from $E_n^{min}$ and the size of the residuals, $r_n$. The shown column vector E is merely an example of selected deviation parameters.

Example 1

In this example, the above algorithm is applied to a system with 24 axial displacements and with three ring-mounted sensors monitoring the magnet position.

Figure 6A:
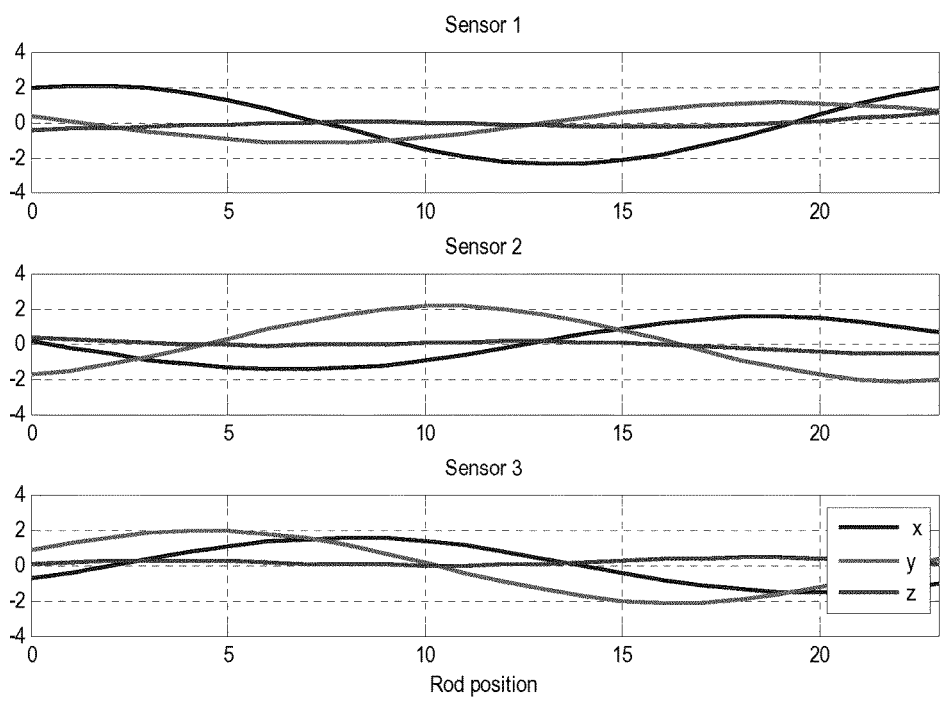
FIG. 6A shows calculated sensor values for a nominal model.

The dipole field model output is derived in each sensors position for magnet that is rotated to a position in 15° steps with 0.1488 mm axial displacement for each step. This can be stored in the system as the nominal model. An example of such a computer generated look-up table is shown in table 1 and illustrated in FIG. 6A.

TABLE 1

Example of look-up table of the nominal model

| Rod position | Angular Pos. (Deg.) | Axial Pos. (mm) | Sensor 1 X | Sensor 1 Y | Sensor 1 Z | Sensor 2 X | Sensor 2 Y | Sensor 2 Z | Sensor 3 X | Sensor 3 Y | Sensor 3 Z |
|---|---|---|---|---|---|---|---|---|---|---|---|
| 0 | 0 | 0.000 | 1.903 | 0.358 | −0.414 | 0.122 | −1.721 | 0.334 | −0.788 | 0.861 | 0.080 |
| 1 | 15 | 0.149 | 2.057 | 0.067 | −0.393 | −0.234 | −1.503 | 0.223 | −0.447 | 1.266 | 0.170 |
| 2 | 30 | 0.298 | 2.072 | −0.232 | −0.342 | −0.583 | −1.168 | 0.116 | −0.066 | 1.600 | 0.226 |
| 3 | 45 | 0.446 | 1.940 | −0.517 | −0.272 | −0.903 | −0.736 | 0.023 | 0.328 | 1.835 | 0.248 |
| 4 | 60 | 0.595 | 1.666 | −0.768 | −0.192 | −1.169 | −0.239 | −0.046 | 0.707 | 1.952 | 0.239 |
| 5 | 75 | 0.744 | 1.267 | −0.968 | −0.116 | −1.364 | 0.290 | −0.088 | 1.041 | 1.939 | 0.204 |
| 6 | 90 | 0.893 | 0.766 | −1.103 | −0.052 | −1.471 | 0.812 | −0.101 | 1.306 | 1.792 | 0.152 |
| 7 | 105 | 1.042 | 0.198 | −1.162 | −0.008 | −1.482 | 1.288 | −0.086 | 1.480 | 1.518 | 0.095 |
| 8 | 120 | 1.190 | −0.398 | −1.141 | 0.010 | −1.394 | 1.683 | −0.051 | 1.549 | 1.134 | 0.041 |
| 9 | 135 | 1.339 | −0.979 | −1.041 | 0.002 | −1.212 | 1.964 | −0.004 | 1.507 | 0.664 | 0.002 |
| 10 | 150 | 1.488 | −1.502 | −0.870 | −0.030 | −0.946 | 2.110 | 0.046 | 1.357 | 0.139 | −0.015 |
| 11 | 165 | 1.637 | −1.928 | −0.640 | −0.080 | −0.614 | 2.109 | 0.087 | 1.109 | −0.403 | −0.007 |
| 12 | 180 | 1.786 | −2.226 | −0.366 | −0.138 | −0.238 | 1.958 | 0.111 | 0.780 | −0.925 | 0.027 |
| 13 | 195 | 1.934 | −2.372 | −0.067 | −0.196 | 0.156 | 1.667 | 0.111 | 0.394 | −1.390 | 0.085 |
| 14 | 210 | 2.083 | −2.354 | 0.234 | −0.241 | 0.542 | 1.257 | 0.082 | −0.020 | −1.763 | 0.159 |
| 15 | 225 | 2.232 | −2.172 | 0.517 | −0.265 | 0.892 | 0.756 | 0.023 | −0.433 | −2.017 | 0.242 |
| 16 | 240 | 2.381 | −1.838 | 0.763 | −0.259 | 1.182 | 0.201 | −0.062 | −0.814 | −2.133 | 0.321 |
| 17 | 255 | 2.530 | −1.376 | 0.954 | −0.219 | 1.391 | −0.367 | −0.167 | −1.137 | −2.103 | 0.386 |
| 18 | 270 | 2.678 | −0.819 | 1.079 | −0.144 | 1.506 | −0.909 | −0.281 | −1.378 | −1.929 | 0.425 |
| 19 | 285 | 2.827 | −0.208 | 1.128 | −0.037 | 1.517 | −1.385 | −0.393 | −1.522 | −1.622 | 0.429 |
| 20 | 300 | 2.976 | 0.413 | 1.100 | 0.095 | 1.425 | −1.760 | −0.489 | −1.558 | −1.206 | 0.394 |
| 21 | 315 | 3.125 | 1.001 | 0.997 | 0.241 | 1.237 | −2.010 | −0.558 | −1.486 | −0.711 | 0.316 |
| 22 | 330 | 3.274 | 1.513 | 0.828 | 0.389 | 0.966 | −2.119 | −0.589 | −1.312 | −0.172 | 0.199 |
| 23 | 345 | 3.422 | 1.913 | 0.604 | 0.525 | 0.633 | −2.079 | −0.574 | −1.051 | 0.372 | 0.049 |

Figure 6B:
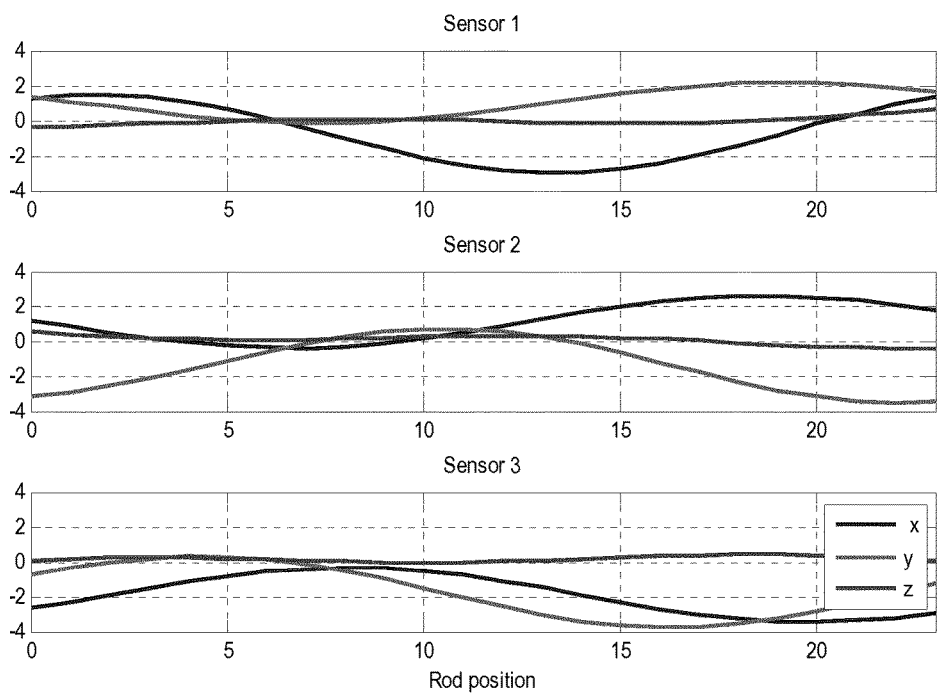
FIG. 6B shows difference between the measured sensor signal and the nominal model.

When a measurement is performed, all sensor values are read from all axes and difference from nominal model is derived as shown in table 2 and illustrated in FIG. 6B.

TABLE 2

Example of measured sensor values for a given position and difference between measured and nominal model.

Readings from sensors in current position

| 7 | 105 | 1.042 | 0.608 | −1.032 | −0.089 | −1.073 | 1.419 | −0.167 | 1.890 | 1.647 | 0.014 |

Difference between measured sensor values and Look-up table values:

| Rod position | Angular Pos. (Deg.) | Axial Pos. (mm) | Sensor 1 X | Sensor 1 Y | Sensor 1 Z | Sensor 2 X | Sensor 2 Y | Sensor 2 Z | Sensor 3 X | Sensor 3 Y | Sensor 3 Z |
|---|---|---|---|---|---|---|---|---|---|---|---|
| 0 | 0 | 0.000 | 1.295 | 1.390 | −0.326 | 1.195 | −3.140 | 0.501 | −2.678 | −0.786 | 0.066 |
| 1 | 15 | 0.149 | 1.450 | 1.099 | −0.305 | 0.839 | −2.922 | 0.391 | −2.338 | −0.381 | 0.156 |
| 2 | 30 | 0.298 | 1.464 | 0.800 | −0.254 | 0.490 | −2.586 | 0.283 | −1.956 | −0.047 | 0.212 |
| 3 | 45 | 0.446 | 1.332 | 0.515 | −0.183 | 0.170 | −2.155 | 0.191 | −1.562 | 0.188 | 0.234 |
| 4 | 60 | 0.595 | 1.059 | 0.264 | −0.104 | −0.096 | −1.658 | 0.121 | −1.183 | 0.305 | 0.224 |
| 5 | 75 | 0.744 | 0.659 | 0.064 | −0.027 | −0.291 | −1.129 | 0.079 | −0.849 | 0.292 | 0.189 |
| 6 | 90 | 0.893 | 0.158 | −0.071 | 0.037 | −0.398 | −0.607 | 0.067 | −0.584 | 0.145 | 0.138 |
| 7 | 105 | 1.042 | −0.410 | −0.130 | 0.081 | −0.409 | −0.131 | 0.081 | −0.411 | −0.129 | 0.080 |
| 8 | 120 | 1.190 | −1.006 | −0.109 | 0.099 | −0.322 | 0.264 | 0.116 | −0.341 | −0.513 | 0.027 |
| 9 | 135 | 1.339 | −1.587 | −0.009 | 0.090 | −0.139 | 0.545 | 0.163 | −0.383 | −0.984 | −0.012 |
| 10 | 150 | 1.488 | −2.110 | 0.162 | 0.059 | 0.126 | 0.692 | 0.213 | −0.533 | −1.508 | −0.030 |
| 11 | 165 | 1.637 | −2.536 | 0.392 | 0.009 | 0.458 | 0.690 | 0.255 | −0.781 | −2.050 | −0.022 |
| 12 | 180 | 1.786 | −2.834 | 0.666 | −0.050 | 0.834 | 0.539 | 0.279 | −1.110 | −2.572 | 0.013 |
| 13 | 195 | 1.934 | −2.980 | 0.964 | −0.107 | 1.229 | 0.248 | 0.278 | −1.496 | −3.037 | 0.070 |
| 14 | 210 | 2.083 | −2.962 | 1.266 | −0.152 | 1.615 | −0.162 | 0.249 | −1.910 | −3.410 | 0.145 |
| 15 | 225 | 2.232 | −2.780 | 1.549 | −0.176 | 1.965 | −0.663 | 0.190 | −2.323 | −3.664 | 0.228 |
| 16 | 240 | 2.381 | −2.446 | 1.795 | −0.170 | 2.255 | −1.218 | 0.105 | −2.704 | −3.780 | 0.307 |
| 17 | 255 | 2.530 | −1.984 | 1.986 | −0.130 | 2.464 | −1.786 | 0.000 | −3.027 | −3.750 | 0.372 |
| 18 | 270 | 2.678 | −1.427 | 2.111 | −0.055 | 2.579 | −2.328 | −0.114 | −3.269 | −3.576 | 0.411 |
| 19 | 285 | 2.827 | −0.816 | 2.160 | 0.052 | 2.590 | −2.804 | −0.225 | −3.412 | −3.270 | 0.415 |
| 20 | 300 | 2.976 | −0.194 | 2.132 | 0.184 | 2.498 | −3.179 | −0.321 | −3.448 | −2.853 | 0.380 |
| 21 | 315 | 3.125 | 0.393 | 2.029 | 0.330 | 2.309 | −3.429 | −0.390 | −3.376 | −2.358 | 0.302 |
| 22 | 330 | 3.274 | 0.905 | 1.859 | 0.478 | 2.039 | −3.537 | −0.421 | −3.202 | −1.819 | 0.185 |
| 23 | 345 | 3.422 | 1.305 | 1.636 | 0.614 | 1.705 | −3.498 | −0.407 | −2.941 | −1.275 | 0.035 |

Then the Deviation parameters are derived by multiplication of $M_n$. This yields the $E_n$-vector for every position. These are listed in table 3.

The deviations are bounded within configurable limits. For instance, $\Delta\varphi$ is bounded within ±7° to avoid that neighbouring positions overlap with the actual position. Furthermore, knowledge of the mechanical constraints of the magnet positions can also be applied at this point to rule out candidates when estimating the position.

TABLE 3

Estimated Deviation parameters for all positions
Estimated deviation of system parameters for all positions

| Rod position | Angular Pos. (Deg.) | Axial Pos. (mm) | $B_{ext}X$ | $B_{ext}Y$ | $B_{ext}Z$ | Magnet position offset X | Magnet position offset Y | Magnet position offset Z | Magnet moment offset | Magnet angle offset | Magnet tilt offset |
|---|---|---|---|---|---|---|---|---|---|---|---|
| 0 | 0 | 0.000 | −1.033 | 2.153 | −0.172 | 0.283 | 0.959 | −1.149 | −2400.000 | 7.000 | −3.517 |
| 1 | 15 | 0.149 | 0.327 | 1.602 | −0.173 | −0.013 | 1.000 | −0.105 | −2400.000 | 7.000 | −3.704 |
| 2 | 30 | 0.298 | 1.151 | 1.661 | −0.174 | −0.254 | 0.967 | 0.368 | −2400.000 | 7.000 | −3.887 |
| 3 | 45 | 0.446 | 5.132 | 3.774 | −0.175 | −0.443 | 0.897 | 2.413 | 2400.000 | 7.000 | −4.066 |
| 4 | 60 | 0.595 | −1.274 | −0.265 | −0.177 | 0.585 | −0.811 | −0.902 | −2400.000 | 7.000 | −4.240 |
| 5 | 75 | 0.744 | −0.120 | 0.207 | −0.178 | 0.674 | −0.739 | −0.328 | −2400.000 | 7.000 | −4.407 |
| 6 | 90 | 0.893 | 0.245 | 0.161 | −0.179 | 0.212 | −0.372 | −0.148 | −625.788 | 7.000 | −4.566 |
| 7 | 105 | 1.042 | 0.385 | −0.346 | −0.180 | −0.992 | −0.122 | −0.073 | −910.524 | −0.345 | −4.716 |
| 8 | 120 | 1.190 | 0.058 | −0.539 | −0.181 | −0.957 | −0.289 | 0.098 | −1760.730 | −7.000 | −4.854 |
| 9 | 135 | 1.339 | −19.517 | −15.929 | −0.182 | −0.905 | −0.425 | 0.227 | −2400.000 | 7.000 | −4.981 |
| 10 | 150 | 1.488 | 5.851 | 1.065 | −0.183 | 0.774 | 0.633 | 0.515 | −2400.000 | −7.000 | −5.000 |
| 11 | 165 | 1.637 | 16.559 | −5.991 | −0.184 | 0.576 | 0.817 | 2.520 | −2400.000 | −7.000 | −5.000 |
| 12 | 180 | 1.786 | −3.412 | 4.909 | −0.184 | −0.335 | −0.942 | −0.900 | −862.746 | −7.000 | −5.000 |
| 13 | 195 | 1.934 | −0.057 | 3.282 | −0.185 | −0.076 | −0.997 | −0.180 | −2400.000 | −7.000 | −5.000 |
| 14 | 210 | 2.083 | 1.642 | 3.270 | −0.185 | 0.181 | −0.983 | 0.400 | −2400.000 | −7.000 | −5.000 |

TABLE 3-continued

Estimated Deviation parameters for all positions
Estimated deviation of system parameters for all positions

| Rod position | Angular Pos. (Deg.) | Axial Pos. (mm) | $B_{ext}X$ | $B_{ext}Y$ | $B_{ext}Z$ | Magnet position offset X | Magnet position offset Y | Magnet position offset Z | Magnet moment offset | Magnet angle offset | Magnet tilt offset |
|---|---|---|---|---|---|---|---|---|---|---|---|
| 15 | 225 | 2.232 | 9.494 | 7.474 | −0.186 | 0.424 | −0.906 | 2.520 | −2400.000 | −7.000 | −5.000 |
| 16 | 240 | 2.381 | −3.054 | −0.447 | −0.186 | −0.642 | 0.767 | −2.468 | −2400.000 | −7.000 | −5.000 |
| 17 | 255 | 2.530 | −0.845 | 0.593 | −0.186 | −0.822 | 0.569 | −1.489 | −2400.000 | −7.000 | −5.000 |
| 18 | 270 | 2.678 | −0.089 | 0.741 | −0.186 | −0.947 | 0.321 | −1.345 | −2400.000 | −7.000 | −5.000 |
| 19 | 285 | 2.827 | 0.413 | 0.236 | −0.185 | −0.364 | −0.042 | −1.773 | −2400.000 | −0.139 | −5.000 |
| 20 | 300 | 2.976 | 0.848 | 1.136 | −0.185 | −0.978 | −0.207 | −1.226 | −2400.000 | 7.000 | −5.000 |
| 21 | 315 | 3.125 | 1.422 | 0.843 | −0.184 | −0.889 | −0.457 | −1.745 | −2400.000 | 7.000 | −5.000 |
| 22 | 330 | 3.274 | 2.528 | 0.353 | −0.184 | −0.748 | −0.664 | −2.520 | −2400.000 | 7.000 | −5.000 |
| 23 | 345 | 3.422 | 10.401 | −3.830 | −0.183 | −0.568 | −0.823 | −2.520 | 2400.000 | 7.000 | −5.000 |

$E_n$ is multiplied with $J_n$ and added to the nominal model giving us the updated version of the nominal model. The residuals between this model and the measured sensor values are derived. These are exemplified in table 4 and FIG. 7 showing the residual error between the updated version of the nominal model and the measured values.

Figure 7:
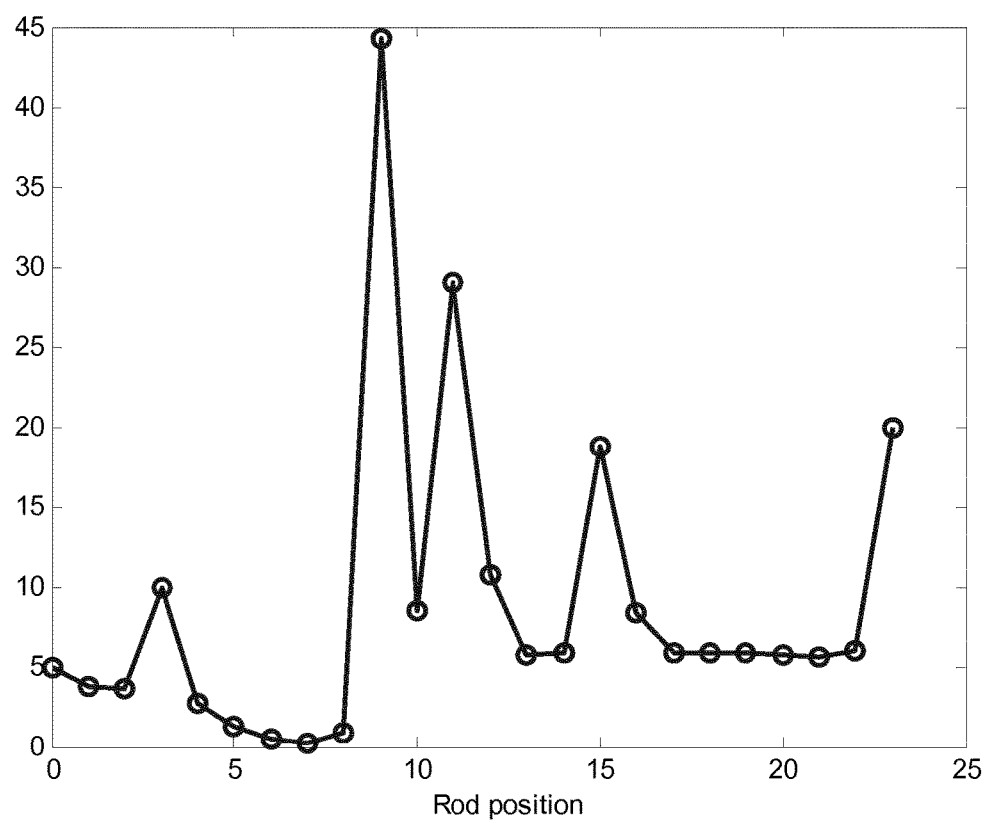
FIG. 7 shows residuals between the nominal model and measured sensor values.

From FIG. 7, it is evident that the algorithm estimated the correct axial position of magnet, i.e. Rod position 7, axial position of 1.042 mm and rotational position of 105°. Table 5 states the deviations of system parameters for that position:

TABLE 4

Calculation of residuals between the updated version of the nominal model and measured values Readings from sensors in current position

| 7 | 105 | 1.042 | 0.608 | −1.032 | −0.089 | −1.073 | 1.419 | −0.167 | 1.890 | 1.647 | 0.014 |

Difference between measured sensor values and linearised corrected values:

| Rod position | Angular Pos. (Deg.) | Axial Pos. (mm) | Sensor 1 X | Sensor 1 Y | Sensor 1 Z | Sensor 2 X | Sensor 2 Y | Sensor 2 Z | Sensor 3 X | Sensor 3 Y | Sensor 3 Z | Sum of deviance: |
|---|---|---|---|---|---|---|---|---|---|---|---|---|
| 0 | 0 | 0.000 | −0.646 | −3.104 | 0.122 | −0.277 | 1.182 | −0.159 | 3.309 | −1.180 | 0.102 | 4.891 |
| 1 | 15 | 0.149 | −1.584 | −2.224 | 0.319 | −1.081 | 1.351 | −0.287 | 1.815 | −0.784 | 0.016 | 3.813 |
| 2 | 30 | 0.298 | −2.020 | −2.066 | 0.366 | −1.434 | 0.858 | −0.216 | 0.859 | −1.020 | −0.107 | 3.621 |
| 3 | 45 | 0.446 | −5.808 | −3.920 | 0.942 | −4.792 | −1.622 | −0.132 | −3.245 | −3.542 | −0.768 | 9.963 |
| 4 | 60 | 0.595 | −0.004 | −0.064 | −0.019 | 1.016 | 1.546 | −0.079 | 1.953 | −0.053 | 0.126 | 2.695 |
| 5 | 75 | 0.744 | −0.647 | −0.278 | 0.060 | −0.069 | 0.806 | −0.064 | 0.599 | −0.207 | 0.012 | 1.249 |
| 6 | 90 | 0.893 | −0.330 | −0.057 | 0.023 | −0.030 | 0.293 | −0.018 | 0.124 | −0.142 | −0.004 | 0.485 |
| 7 | 105 | 1.042 | −0.003 | 0.072 | 0.000 | −0.006 | 0.090 | −0.004 | 0.022 | 0.101 | 0.005 | 0.155 |
| 8 | 120 | 1.190 | 0.384 | 0.253 | −0.009 | 0.065 | 0.228 | −0.004 | 0.229 | 0.561 | 0.016 | 0.797 |
| 9 | 135 | 1.339 | 20.780 | 15.509 | −0.042 | 19.116 | 15.344 | −0.006 | 19.853 | 16.951 | 0.049 | 44.212 |
| 10 | 150 | 1.488 | −3.753 | −1.209 | −0.088 | −5.635 | −1.368 | 0.042 | −4.791 | 0.409 | 0.049 | 8.504 |
| 11 | 165 | 1.637 | −14.243 | 5.508 | −0.624 | −16.683 | 5.530 | 0.584 | −15.408 | 7.693 | 0.045 | 28.973 |
| 12 | 180 | 1.786 | 5.753 | −5.197 | 0.382 | 2.503 | −5.095 | −0.395 | 4.244 | −2.283 | 0.022 | 10.764 |
| 13 | 195 | 1.934 | 2.570 | −3.782 | 0.214 | −1.081 | −2.976 | −0.186 | 1.463 | −0.182 | −0.014 | 5.761 |
| 14 | 210 | 2.083 | 1.171 | −4.055 | 0.101 | −2.944 | −2.719 | −0.099 | 0.285 | 0.201 | 0.014 | 5.832 |
| 15 | 225 | 2.232 | −6.587 | −8.649 | −0.436 | −10.994 | −6.739 | −0.062 | −7.127 | −3.862 | 0.517 | 18.725 |
| 16 | 240 | 2.381 | 4.908 | −1.121 | 0.756 | 0.809 | 1.475 | 0.105 | 5.108 | 3.731 | −0.837 | 8.335 |
| 17 | 255 | 2.530 | 2.359 | −2.188 | 0.398 | −1.664 | 1.149 | 0.291 | 3.235 | 2.959 | −0.663 | 5.860 |
| 18 | 270 | 2.678 | 1.327 | −2.332 | 0.244 | −2.477 | 1.643 | 0.485 | 2.862 | 2.941 | −0.701 | 5.802 |
| 19 | 285 | 2.827 | 0.373 | −2.027 | 0.073 | −2.725 | 2.487 | 0.712 | 2.734 | 2.915 | −0.764 | 5.910 |
| 20 | 300 | 2.976 | −0.657 | −2.724 | −0.155 | −2.955 | 2.285 | 0.759 | 2.516 | 1.743 | −0.571 | 5.665 |
| 21 | 315 | 3.125 | −1.435 | −2.393 | −0.361 | −3.128 | 2.468 | 0.890 | 1.907 | 1.466 | −0.493 | 5.533 |
| 22 | 330 | 3.274 | −2.716 | −1.856 | −0.666 | −3.839 | 2.632 | 1.002 | 0.577 | 1.307 | −0.294 | 6.005 |
| 23 | 345 | 3.422 | −11.383 | 2.182 | −1.015 | −11.606 | 7.081 | 1.004 | −7.295 | 4.751 | 0.063 | 19.925 |

TABLE 5

Deviation of system parameters for estimated position
Estimated deviation of system parameters for estimated position

| Rod position | Angular Pos. (Deg.) | Axial Pos. (mm) | $B_{ext}X$ | $B_{ext}Y$ | $B_{ext}Z$ | Magnet position offset X | Magnet position offset Y | Magnet position offset Z | Magnet moment offset | Magnet angle offset | Magnet tilt offset |
|---|---|---|---|---|---|---|---|---|---|---|---|
| 7 | 105 | 1.042 | 0.385 | −0.346 | −0.180 | −0.992 | −0.122 | −0.073 | −910.524 | −0.345 | −4.716 |

From the table, it is possible to evaluate the quality of the algorithm output. For example, the uniform external field is estimated to a have a magnitude of 0.55 Gauss (derived from the first three components). This is in the range of the earth's magnetic field. However, if this was estimated to be e.g. 2 Gauss, it would be more likely that the algorithm has estimated an incorrect position or that a large external field would be present.

The magnet position has radial offset in the x-direction of −0.992 mm. If this is an unrealistic mechanical offset, an implemented system could be programmed to reject the algorithm output. Thus, if the fail-safe measures are not violated, the estimated position is considered a correct position.

If the risk of external magnetic fields other than earth's magnetic field and disturbances in the internal magnetic field by the presence of iron nearby can be positively excluded, the most likely candidate of actual position found in the table can be relayed or displayed as actual position. However, in most applications the risk of disturbances in the magnetic field must be considered likely from a variety of sources and in some applications the consequences of a wrong determination of position could have serious and unacceptable consequences. In such applications a number of fail-safe measures can be taken, for example:

(1) Taking a number of readings and use mean axis value from each axis from each sensor only when variations between readings are less than a predefined level. This could prevent wrong readings from the sensors caused by a fluctuating disturbance in the magnetic field.

(2) Subtracting readings from diametrically opposite sensors to eliminate the magnet field contribution and the homogenous external field contribution and hence calculate the gradient of an inhomogeneous external field. Comparison against threshold values may be used as criteria for using the readings.

(3) Using readings to calculate the external field. Comparison against threshold values may be used as criteria for using the readings.

(4) Using readings from an over-determined sensor configuration to calculate deviations from pre-determined nominal mechanical geometry and magnet characteristics. Comparison against threshold values may be used as criteria for using the readings.

(5) Comparing the deviance of the most likely position and the deviances of rejected positions (e.g. the second most likely position) to determine the credibility of the most likely position. Comparison against threshold values may be used as criteria for using the readings.

(6) Comparing the most likely position and rejected positions, e.g. the top 10 next most likely positions, to determine the distribution of the positions. The distribution, e.g. span between minimum and maximum position, may be used as criteria for using the readings.

(7) Using the most likely position to calculate the field contribution from the magnet and subtracting the contribution from the readings to obtain an estimated external field. The estimated external field may be used as input for calculating a most likely position which should be rejected by one or more of the fail-safe measures since the field contribution from the magnet has been eliminated. The field contribution from a position different from the most likely positions may be calculated and added to the estimated external field. The resulting field may be used as input for calculating a most likely position. Correspondence between the selected position and calculated position may be used as criteria for using the readings.

(8) Using calculated positions to determine the mechanical movement, e.g. direction, speed and position stability. Comparison against threshold values may be used as criteria for using the readings.

(9) Only appoint a most likely candidate of actual position if the minimum sum of deviance is less than a predefined value, to ensure a certain level of coherence between measured values and (expected) table values. This predefined value may be dependent on where in the range of operation the most likely candidate is, since the distances between neighboring candidates vary with distance from sensor. This should prevent a constant disturbance above a certain magnitude from causing the wrong position to be appointed most likely candidate and can also prevent a most likely candidate from being appointed if one of the sensors axis' have gone into saturated mode. If sensors are exposed to a magnetic field of a strength exceeding their limit of operation, they will go into saturation mode and give a readout of (a known predefined) maximum value.

The above mentioned fail-safe measures will only be able to help prevent read-out of false positions by giving no position read-out at all. The system can then (if change of position is either prevented or monitored not to occur) repeat measurements until the system is clear of the external disturbance of the internal magnetic field. If change of position cannot be prevented, it can be monitored and the next successful read-out can be accompanied with a notification that current position is the sum of two (or more) individual movements. In some situations the system may be able to perform correct read-outs even if subjected to a disturbance in the internal magnetic field. Two such situations are described in the following.

(10) If a very local disturbance occurs (as described above in point 3), typically caused by a small magnet or piece of iron very close to some of the sensors, it may be possible in some situations to get a valid reading instead of a fail-safe voided reading.

(11) In some applications of such a system, the change of position between measurements is limited and in such application knowledge of prior position reading may help prevent false readouts of fail-safe situations. In disposable injection devices with the threaded rod connected to a reservoir piston, movement is only possible in one direction. Furthermore a dose pre-adjustment device limits each injection to a certain maximum travel of the tracing magnet. If a position measurement is performed after each injection, the most likely candidate found should be within the limited travel of the trace magnet or a disturbance must be assumed to have interfered with the measurement. The system can then either fail safely and not perform a read-out or find the second-most likely candidate, which is within the expected range. The validity should then be checked by use of a reduced threshold value of least sum of deviance (within valid range) and may be supplied by a coherence-check of the individual sensors best-fit values.

Alternatively the limited allowable movement can be used to reduce the number of calculations and perform fewer table look-up operations, thereby increasing calculation speed and reducing power consumption.

In FIG. 1 a further exemplary embodiment of a sensor assembly is configured as a number of sensors are placed along the line of movement. In the following a second exemplary algorithm for estimating a current position and orientation of a magnet will be described.

Figure 8A:
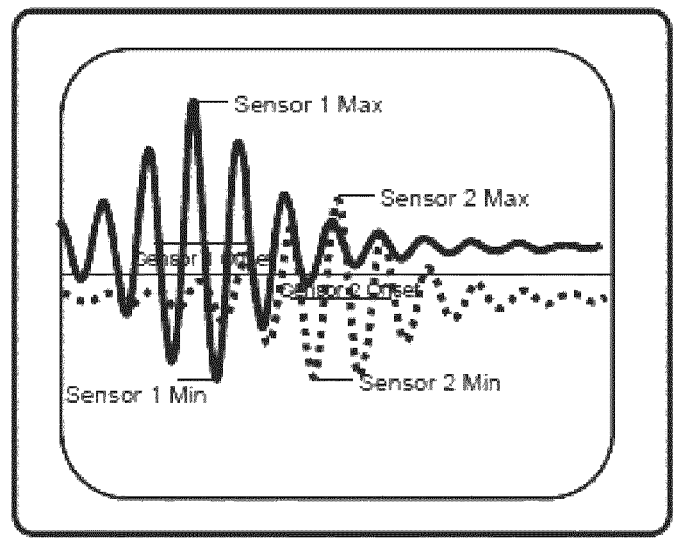
FIGS. 8A and 8B show sensor gain adjustments.
Figure 8B:
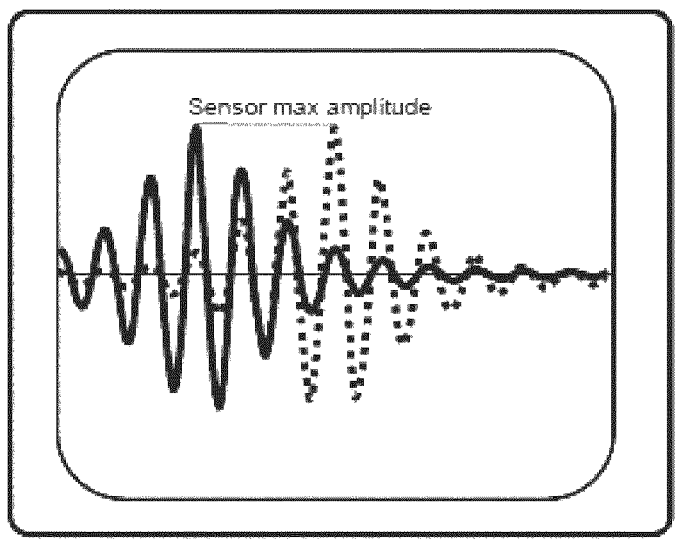

Each 3D magnetometer will measure with different off-sets in the three different directions and to compensate and adjust for the described embodiment, a reference magnet on a reference threaded rod is moved through the entire range of operation and readings of all axis' from all the sensors taken at small intervals of angular rotation of the threaded rod. All axis readings from all sensors are then offset and gain adjusted, so that maximum amplitude reached for each sensor is the same for all sensors and directions and they all fluctuate symmetrically around zero. This is illustrated in FIGS. 8A and 8B showing sensor gain optimization, but only for one axis and two sensors to provide a better understanding through simplicity.

Sensor 1 maximum amplitude: $(S1_{Max}-S1_{Min})/2$
Sensor 2 maximum amplitude: $(S2_{Max}-S2_{Min})/2$
Maximum amplitude: Sensor 1 maximum
Sensor 1 gain: 1
Sensor 2 gain: Sensor 1 maximum amplitude/Sensor 2 maximum amplitude (>1)
Sensor 1 off-set: Sensor 1 maximum amplitude–sensor 1 maximum
Sensor 2 off-set: Sensor 2 maximum amplitude–sensor 2 maximum With a compensated and adjusted system, the axis values for each axis from each sensor can then be measured at small increments of angular rotation of the rod and, consequently, small steps of linear motion caused by the threading.

Figure 9:
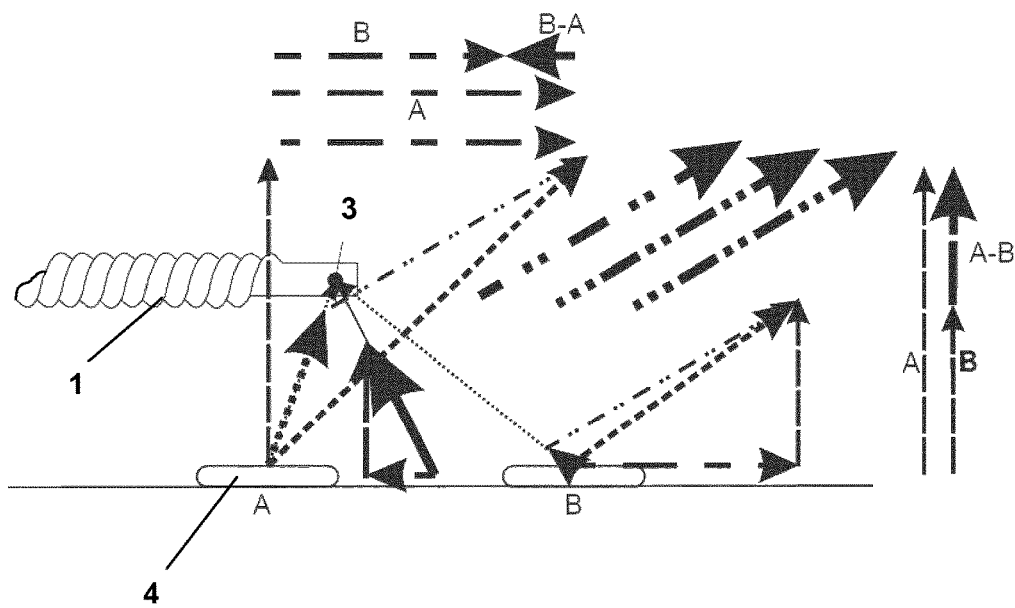
FIG. 9 shows vector compensation for earth's magnetic field.

To compensate for earth's magnetic field and other disturbing magnetic fields that influence the system with a uniform magnetic field, the axis value from one sensor is subtracted from the value of the value of the parallel axis of the neighboring sensor as illustrated in FIG. 9 showing subtraction of axis values between two sensors to compensate for earth's magnetic field and in which:

Dotted lines: Contributions from magnet
Two-dots-one-line: Earth's magnetic field
Broken line: Resulting vectors from sensors
Long-short line: X-composants of resulting vectors
Long-long: Z-composants of resulting vectors
Full line: Resulting Difference vector
Dotted lines represent distance/direction
Full lines represent amplitude (Increasing with decreasing distance)

Figure 10:
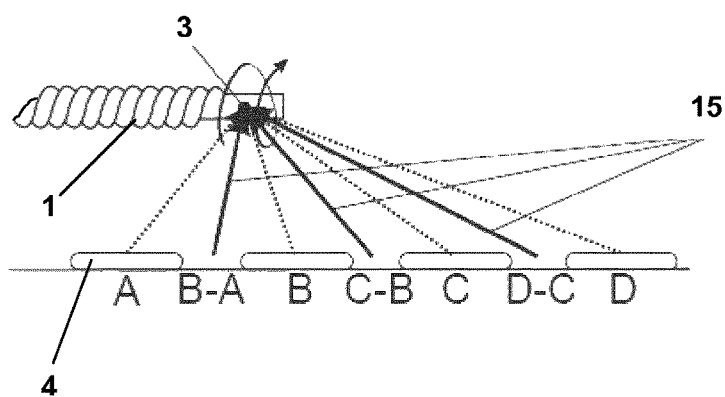
FIG. 10 shows a plurality of difference vectors.

Since the measured axis value in each direction for each sensor represents a vector representing direction and amplitude of the resulting magnetic field the sensor is subjected to, these vectors will represent the sum of the magnetic field of the tracing magnet and earth's magnetic field, which is depending on geographic location and orientation of the system relative to the surface of the earth. Since the contribution of earth's magnetic field must be considered uniform within the small area of the sensors, all sensors will be influenced by the same direction and amplitude from earth's magnetic field. By subtracting the axis values from each other between each sensor, the contribution of earth's magnetic field is cancelled out. This means that from a number (N) of sensors, there will be N−1 difference vectors as illustrated in FIG. 10.

Example 2

For a model corresponding to FIG. 1 with two axially arranged sensors, a piston rod was rotated from 0-150° and measurements were made for every 7.5° of rotation. The measurements listed below in tables 1 and 2 were made using an experimental set-up using Honeywell HMC5883L 3-axis magneto sensors. Based on this, a table of all axis values of all difference vectors for each measured angular (and thus linear) position can then be set up for the entire range of operation and stored in the system. An example of such a table is shown in table 1.

TABLE 6

Example of look-up table of difference-vector axis' values and corresponding positions of a threaded rod

| Rod Position (x 0.5 units) | Angular Pos. (Deg.) | Axial Pos. (mm) | Sensor 1 X | Sensor 1 Y | Sensor 1 Z | Sensor 2 X | Sensor 2 Y | Sensor 2 Z | Difference 2-1 X | Difference 2-1 Y | Difference 2-1 Z |
|---|---|---|---|---|---|---|---|---|---|---|---|
| 0 | 0.0 | 0.000 | −155.9 | 143.2 | 295.9 | −133.7 | 93.8 | 170.2 | 22.2 | −49.4 | −125.7 |
| 1 | 7.5 | 0.074 | −156.6 | 143.5 | 295.9 | −133.4 | 94.3 | 169.9 | 23.2 | −49.2 | −126.0 |
| 2 | 15.0 | 0.149 | −156.7 | 144.2 | 295.1 | −133.2 | 95.2 | 168.7 | 23.5 | −49.0 | −126.4 |
| 3 | 22.5 | 0.223 | −156.6 | 143.8 | 294.5 | −134.4 | 94.2 | 169.7 | 22.2 | −49.6 | −124.8 |
| 4 | 30.0 | 0.298 | −156.1 | 144.3 | 294.0 | −134.6 | 92.9 | 167.3 | 21.5 | −51.4 | −126.7 |
| 5 | 37.5 | 0.372 | −156.4 | 143.4 | 293.7 | −134.7 | 93.8 | 167.0 | 21.7 | −49.6 | −126.7 |
| 6 | 45.0 | 0.446 | −156.9 | 143.4 | 293.2 | −136.0 | 93.1 | 166.0 | 20.9 | −50.3 | −127.2 |
| 7 | 52.5 | 0.521 | −157.2 | 142.8 | 293.3 | −135.7 | 93.1 | 166.2 | 21.5 | −49.7 | −127.1 |
| 8 | 60.0 | 0.595 | −157.3 | 142.7 | 293.3 | −134.6 | 91.2 | 165.4 | 22.7 | −51.5 | −127.9 |
| 9 | 67.5 | 0.670 | −157.0 | 142.6 | 293.9 | −136.2 | 90.5 | 164.3 | 20.8 | −52.1 | −129.6 |
| 10 | 75.0 | 0.744 | −156.6 | 142.2 | 293.0 | −135.0 | 91.6 | 164.8 | 21.6 | −50.6 | −128.2 |
| 11 | 82.5 | 0.818 | −156.4 | 141.6 | 293.4 | −136.1 | 89.7 | 164.9 | 20.3 | −51.9 | −128.5 |
| 12 | 90.0 | 0.893 | −156.5 | 140.8 | 293.4 | −135.9 | 87.9 | 164.5 | 20.6 | −52.9 | −128.9 |

TABLE 6-continued

Example of look-up table of difference-vector axis' values and corresponding positions of a threaded rod

| Rod Position (x 0.5 units) | Angular Pos. (Deg.) | Axial Pos. (mm) | Sensor 1 X | Sensor 1 Y | Sensor 1 Z | Sensor 2 X | Sensor 2 Y | Sensor 2 Z | Difference 2-1 X | Difference 2-1 Y | Difference 2-1 Z |
|---|---|---|---|---|---|---|---|---|---|---|---|
| 13 | 97.5  | 0.967 | −156.8 | 141.3 | 293.4 | −135.9 | 88.2 | 164.7 | 20.9 | −53.1 | −128.7 |
| 14 | 105.0 | 1.042 | −156.6 | 140.2 | 292.7 | −135.3 | 87.2 | 164.9 | 21.3 | −53.0 | −127.8 |
| 15 | 112.5 | 1.116 | −156.8 | 139.5 | 293.4 | −135.7 | 86.7 | 165.4 | 21.1 | −52.8 | −128.0 |
| 16 | 120.0 | 1.190 | −156.9 | 139.9 | 293.0 | −135.0 | 85.4 | 165.0 | 21.9 | −54.5 | −128.0 |
| 17 | 127.5 | 1.265 | −156.1 | 140.5 | 293.2 | −135.1 | 84.8 | 165.0 | 21.0 | −55.7 | −128.2 |
| 18 | 135.0 | 1.339 | −155.7 | 139.2 | 293.1 | −134.8 | 84.7 | 165.8 | 20.9 | −54.5 | −127.3 |
| 19 | 142.5 | 1.414 | −156.0 | 139.5 | 293.0 | −133.7 | 84.0 | 166.0 | 22.3 | −55.5 | −127.0 |
| 20 | 150.0 | 1.488 | −155.6 | 138.5 | 293.0 | −134.3 | 83.8 | 166.1 | 21.3 | −54.7 | −126.9 |

When an actual (current) measurement is performed, all axis values are read from all sensors and the resulting difference-vector axis' values are calculated. Each of these calculated difference values are then subtracted from each of the corresponding table values for each sensor and the results from each axis and each sensor is added to each other for all table values of positions as shown in table 2.

TABLE 7

Calculation of sum of deviance between table values and measured values

Look-up table values:

| Rod Position (x 0.5 units) | Angular Pos. (Deg.) | Axial Pos. (mm) | Sensor 1 X | Sensor 1 Y | Sensor 1 Z | Sensor 2 X | Sensor 2 Y | Sensor 2 Z | Sensor 3 X | Sensor 3 Y | Sensor 3 Z |
|---|---|---|---|---|---|---|---|---|---|---|---|
| 0  | 0.0   | 0.000 | −155.9 | 143.2 | 295.9 | −133.7 | 93.8 | 170.2 | −126.4 | 85.0 | −74.8 |
| 1  | 7.5   | 0.074 | −156.6 | 143.5 | 295.9 | −133.4 | 94.3 | 169.9 | −127.0 | 85.2 | −76.2 |
| 2  | 15.0  | 0.149 | −156.7 | 144.2 | 295.1 | −133.2 | 95.2 | 168.7 | −127.8 | 85.4 | −77.7 |
| 3  | 22.5  | 0.223 | −156.6 | 143.8 | 294.5 | −134.4 | 94.2 | 169.7 | −128.8 | 84.0 | −78.3 |
| 4  | 30.0  | 0.298 | −156.1 | 144.3 | 294.0 | −134.6 | 92.9 | 167.3 | −129.9 | 84.3 | −80.2 |
| 5  | 37.5  | 0.372 | −156.4 | 143.4 | 293.7 | −134.7 | 93.8 | 167.0 | −131.0 | 82.8 | −83.1 |
| 6  | 45.0  | 0.446 | −156.9 | 143.4 | 293.2 | −136.0 | 93.1 | 166.0 | −132.0 | 82.0 | −83.7 |
| 7  | 52.5  | 0.521 | −157.2 | 142.8 | 293.3 | −135.7 | 93.1 | 166.2 | −131.9 | 80.4 | −84.4 |
| 8  | 60.0  | 0.595 | −157.3 | 142.7 | 293.3 | −134.6 | 91.2 | 165.4 | −133.4 | 79.2 | −84.0 |
| 9  | 67.5  | 0.670 | −157.0 | 142.6 | 293.9 | −136.2 | 90.5 | 164.3 | −134.5 | 77.2 | −85.7 |
| 10 | 75.0  | 0.744 | −156.6 | 142.2 | 293.0 | −135.0 | 91.6 | 164.8 | −133.8 | 76.0 | −86.4 |
| 11 | 82.5  | 0.818 | −156.4 | 141.6 | 293.4 | −136.1 | 89.7 | 164.9 | −134.3 | 73.8 | −87.0 |
| 12 | 90.0  | 0.893 | −156.5 | 140.8 | 293.4 | −135.9 | 87.9 | 164.5 | −133.8 | 72.0 | −87.4 |
| 13 | 97.5  | 0.967 | −156.8 | 141.3 | 293.4 | −135.9 | 88.2 | 164.7 | −134.5 | 71.4 | −87.1 |
| 14 | 105.0 | 1.042 | −156.6 | 140.2 | 292.7 | −135.3 | 87.2 | 164.9 | −133.7 | 68.3 | −87.1 |
| 15 | 112.5 | 1.116 | −156.8 | 139.5 | 293.4 | −135.7 | 86.7 | 165.4 | −133.7 | 67.5 | −87.5 |
| 16 | 120.0 | 1.190 | −156.9 | 139.9 | 293.0 | −135.0 | 85.4 | 165.0 | −133.1 | 66.0 | −86.6 |
| 17 | 127.5 | 1.265 | −156.1 | 140.5 | 293.2 | −135.1 | 84.8 | 165.0 | −131.9 | 64.1 | −84.7 |
| 18 | 135.0 | 1.339 | −155.7 | 139.2 | 293.1 | −134.8 | 84.7 | 165.8 | −130.5 | 61.7 | −84.5 |
| 19 | 142.5 | 1.414 | −156.0 | 139.5 | 293.0 | −133.7 | 84.0 | 166.0 | −129.7 | 60.6 | −83.8 |
| 20 | 150.0 | 1.488 | −155.6 | 138.5 | 293.0 | −134.3 | 83.8 | 166.1 | −129.0 | 60.4 | −82.6 |

Readings from sensors in current position

| 8 | 60 | 8.9 | −157.1 | 142.6 | 293.4 | −134.8 | 91.4 | 165.6 | −133.4 | 79.2 | −84.0 |

| | Look-up table values: | | | | | | Measured difference vector compared to look-up table | | | Measured difference vector compared to look-up table | | | Finding least |
|---|---|---|---|---|---|---|---|---|---|---|---|---|---|
| Rod Position | Difference 2-1 X | Difference 2-1 Y | Difference 2-1 Z | Difference 3-2 X | Difference 3-2 Y | Difference 3-2 Z | Deviance 2-1 X | Deviance 2-1 Y | Deviance 2-1 Z | Deviance 3-2 X | Deviance 3-2 Y | Deviance 3-2 Z | deviance: Sum of deviance: |
| 0  | 22.2 | −49.4 | −125.7 | 7.3 | −8.8  | −245.0 | −0.1 | 1.8  | 2.1  | 5.9  | 3.4  | 4.6  | 17.7 |
| 1  | 23.2 | −49.2 | −126.0 | 6.4 | −9.1  | −246.1 | 0.9  | 2.0  | 1.8  | 5.0  | 3.1  | 3.5  | 16.3 |
| 2  | 23.5 | −49.0 | −126.4 | 5.4 | −9.8  | −246.4 | 1.2  | 2.2  | 1.4  | 4.0  | 2.4  | 3.2  | 14.4 |
| 3  | 22.2 | −49.6 | −124.8 | 5.6 | −10.2 | −248.0 | −0.1 | 1.6  | 3.0  | 4.2  | 2.0  | 1.6  | 12.3 |
| 4  | 21.5 | −51.4 | −126.7 | 4.7 | −8.6  | −247.5 | −0.8 | −0.2 | 1.1  | 3.3  | 3.6  | 2.1  | 9.1  |
| 5  | 21.7 | −49.6 | −126.7 | 3.7 | −11.0 | −250.1 | −0.6 | 1.6  | 1.1  | 2.3  | 1.2  | −0.5 | 5.1  |
| 6  | 20.9 | −50.3 | −127.2 | 4.0 | −11.1 | −249.7 | −1.4 | 0.9  | 0.6  | 2.6  | 1.1  | −0.1 | 3.7  |
| 7  | 21.5 | −49.7 | −127.1 | 3.8 | −12.7 | −250.6 | −0.8 | 1.5  | 0.7  | 2.4  | −0.5 | −1.0 | 2.3  |
| 8  | 22.7 | −51.5 | −127.9 | 1.2 | −12.0 | −249.4 | 0.4  | −0.3 | −0.1 | −0.2 | 0.2  | 0.2  | 0.2  |
| 9  | 20.8 | −52.1 | −129.6 | 1.7 | −13.3 | −250.0 | −1.5 | −0.9 | −1.8 | 0.3  | −1.1 | −0.4 | −5.4 |
| 10 | 21.6 | −50.6 | −128.2 | 1.2 | −15.6 | −251.2 | −0.7 | 0.6  | −0.4 | −0.2 | −3.4 | −1.6 | −5.7 |
| 11 | 20.3 | −51.9 | −128.5 | 1.8 | −15.9 | −251.9 | −2.0 | −0.7 | −0.7 | 0.4  | −3.7 | −2.3 | −9.0 |

TABLE 7-continued

Calculation of sum of deviance between table values and measured values

| 12 | 20.6 | −52.9 | −128.9 | 2.1 | −15.9 | −251.9 | −1.7 | −1.7 | −1.1 | 0.7 | −3.7 | −2.3 | −9.8 |
|---|---|---|---|---|---|---|---|---|---|---|---|---|---|
| 13 | 20.9 | −53.1 | −128.7 | 1.4 | −16.8 | −251.8 | −1.4 | −1.9 | −0.9 | 0.0 | −4.6 | −2.2 | −11.0 |
| 14 | 21.3 | −53.0 | −127.8 | 1.6 | −18.9 | −252.0 | −1.0 | −1.8 | 0.0 | 0.2 | −6.7 | −2.4 | −11.7 |
| 15 | 21.1 | −52.8 | −128.0 | 2.0 | −19.2 | −252.9 | −1.2 | −1.6 | −0.2 | 0.6 | −7.0 | −3.3 | −12.7 |
| 16 | 21.9 | −54.5 | −128.0 | 1.9 | −19.4 | −251.6 | −0.4 | −3.3 | −0.2 | 0.5 | −7.2 | −2.0 | −12.6 |
| 17 | 21.0 | −55.7 | −128.2 | 3.2 | −20.7 | −249.7 | −1.3 | −4.5 | −0.4 | 1.8 | −8.5 | −0.1 | −13.0 |
| 18 | 20.9 | −54.5 | −127.3 | 4.3 | −23.0 | −250.3 | −1.4 | −3.3 | 0.5 | 2.9 | −10.8 | −0.7 | −12.8 |
| 19 | 22.3 | −55.5 | −127.0 | 4.0 | −23.4 | −249.8 | 0.0 | −4.3 | 0.8 | 2.6 | −11.2 | −0.2 | −12.3 |
| 20 | 21.3 | −54.7 | −126.9 | 5.3 | −23.4 | −248.7 | −1.0 | −3.5 | 0.9 | 3.9 | −11.2 | 0.9 | −10.0 |

| Calculation of difference vectors in current position: | | | | | | | Finding least deviance between measured position and look-up table values: | | | | | Minimum sum of Deviance: |
|---|---|---|---|---|---|---|---|---|---|---|---|---|
| 8 | 22.3 | −51.2 | −127.8 | 1.4 | −12.2 | −249.6 | 0.4 | −0.3 | −0.1 | −0.2 | 0.2 | 0.2 | 0.2 |

The lowest sum of deviance can now be determined and the corresponding position of the threaded rod is considered most likely candidate for the actual position of the threaded rod. This method will in effect ensure that the difference values from the sensor-pair(s) closest to the actual position of the tracing magnet will be the determining sensors, since the amplitude of the signal from these sensors will be orders of magnitudes higher than the sensor further from the tracing magnet. As appears, it was possible to identify the correct position although the measured values were not 100% identical to those stored in the look-up table.

Figure 11A:
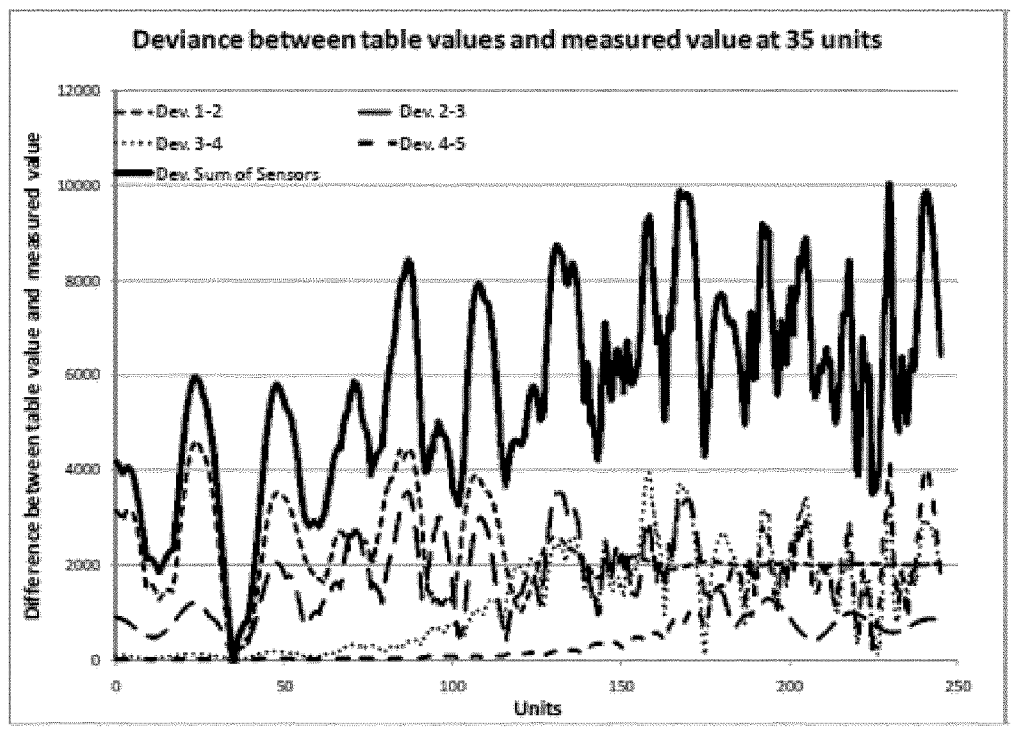
FIGS. 11A and 11B show deviance graphs between table and measured values.
Figure 11B:
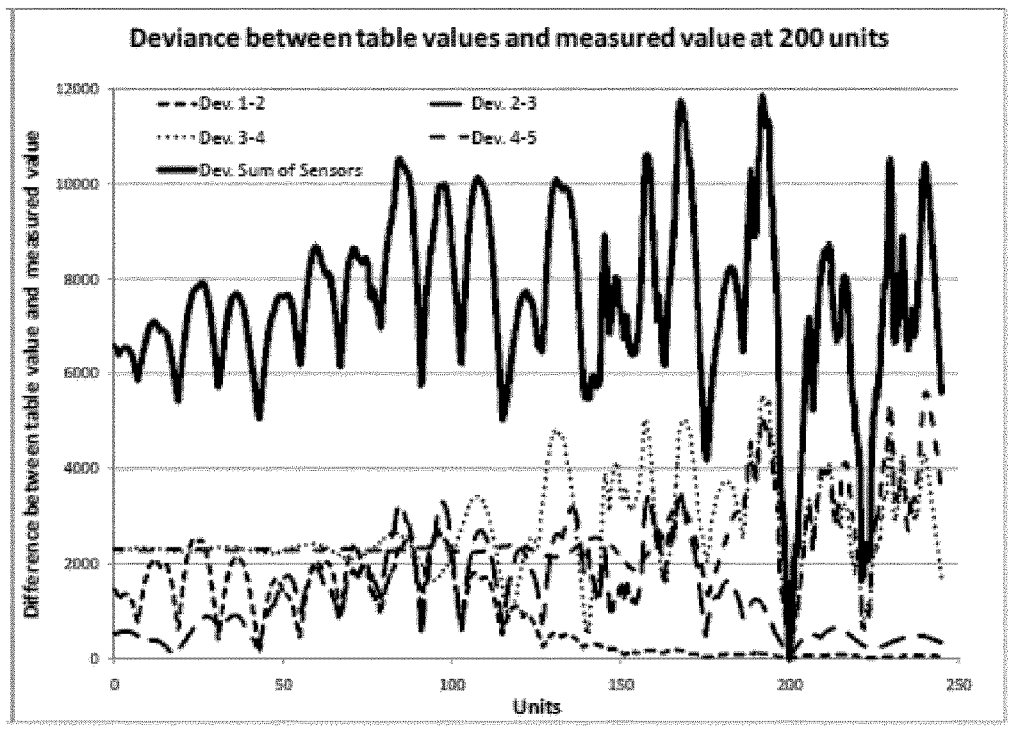
Figure 12A:
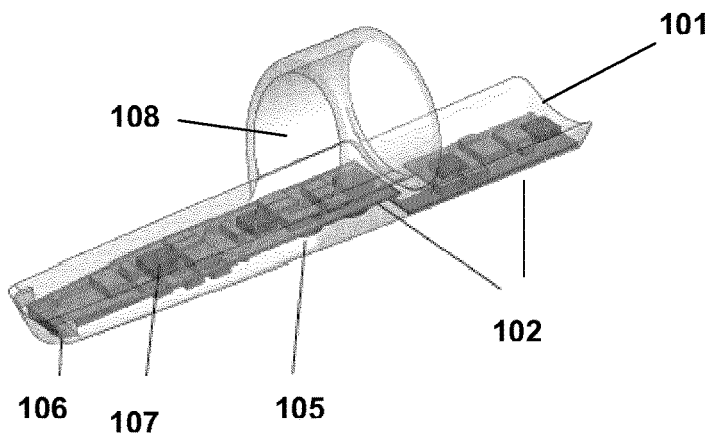
FIGS. 12A-12D show views of a first embodiment of a measuring system for a drug device.
Figure 12B:
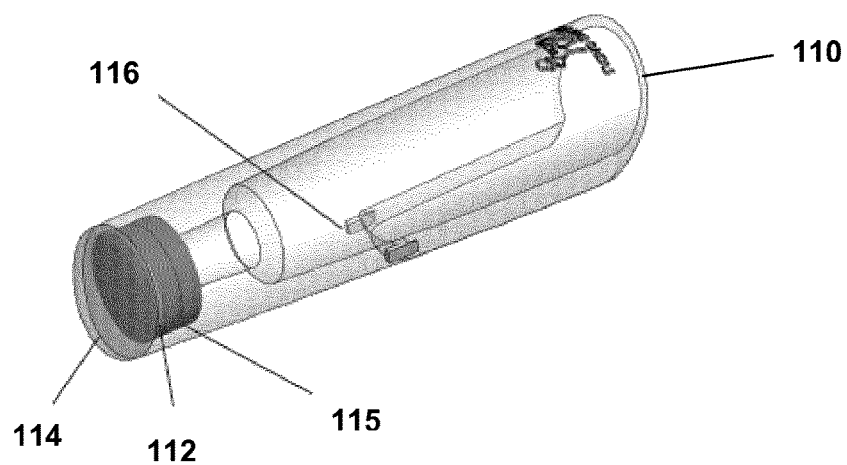
Figure 12C:
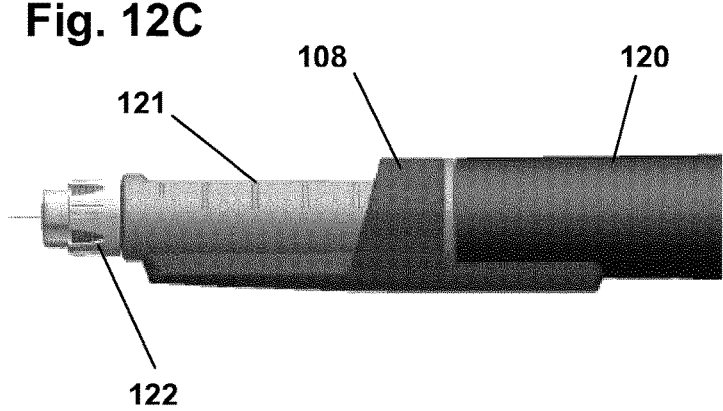
Figure 12D:

The contribution to the sum of deviance from the closest sensors will thus increase significantly on each side of the correct value and by far overrule if the contribution to the sum of deviance from some of the sensors further away should have a minimum elsewhere. This is illustrated in FIGS. 11A and 11B where the poorer signal-to-noise ratio for the sensor furthest from the trace magnets actual position leads to a minimum contribution to the sum of deviance on a position other than the actual position. In FIG. 11A the position of the magnet corresponds to a drug delivery system of the traditional pen-type in which 35 units of drug has been expelled from a cartridge comprising 300 units of drug. FIG. 11B illustrates corresponding measurements when 200 units have been expelled.

For an exemplary application of the invention in a drug delivery system for detection of expelled amounts of drug the following considerations are relevant. Firstly, the drug delivery system should comprise a component which is moved both axially and rotationally during an operation associated with the expelling of a dose of drug. Such a system could be a pen-formed drug delivery device in which a piston rod corresponding to a set dose is moved both axially and rotationally to move the piston of a drug-filled cartridge forwards to thereby expel the set dose of drug there from, this corresponding to the above-described two examples.

An example of such a drug delivery device is FlexTouch® from Novo Nordisk. When provided with a 3 ml Penfill® cartridge containing a 100 IU/ml insulin formulation the FlexTouch® device is set to axially move forward the piston rod 0.1488 mm for each IU to be expelled, this corresponding to 15° of rotation of the piston rod. Thus, in order to provide a measuring system configured to detect the position of the piston rod with a precision corresponding to 0.5 IU it should be possible to detect the axial position with a precision corresponding to 7.5° of rotation of the piston rod.

As indicated, the above-described exemplary systems have been set up for application in a drug delivery system. Correspondingly, in the following a number of different configurations for a combined system comprising a pen-formed drug delivery device (e.g. a FlexTouch® or a Flex-Pen® from Novo Nordisk, see e.g. U.S. Pat. No. 6,004,297 which is hereby incorporated by reference) and a measuring system for detection of an out-dosed amount of drug will be described. As FlexTouch® and FlexPen® are pre-filled drug delivery pens designed to be disposed off when the drug cartridge has been emptied, the measuring system is provided as a re-useable durable add-on system/unit adapted to be used in combination with a corresponding pen, i.e. the pen comprising a small magnet mounted distally on the piston rod and coupling means allowing the measuring magnetometers to be positioned in a pre-determined position relative to the piston rod. In order to determine an amount of drug expelled, the position of the piston rod before and after an expelling action is detected, the difference there between corresponding to the axial displacement of the piston rod during out-dosing of a given amount of drug and thus the axial displacement of the piston in the cartridge. From the axial distance traveled by the piston rod an amount of drug can be calculated (e.g. each 0.1488 mm of travel representing 1 IU of insulin) and communicated to the user and/or stored in a memory together with other data such as time and date.

Turning to FIGS. 12A-12D a measuring system is shown configured as a two-unit assembly comprising a measuring unit 101 and a display unit 110, the measuring unit being adapted to be mounted on a drug delivery pen 120 for the life of the pen for thereafter being transferred to a new pen, the display unit being configured as a cap adapted to cover the needle mount (and a needle assembly 122 if mounted) and thus adapted to be removed prior to administration of a dose of drug and re-mounted after the administration. Correspondingly, the positions of the piston rod when the cap is removed respectively attached again can be used to calculate an expelled dose of drug which is then shown together with a time stamp on the display unit. Indeed, if the cap is left off between two dosing events then a combined dose will be registered. However, as this would be associated with a long period of time between two measurements the processor could be programmed to provide a warning if the cap has been left off for a period of time longer than necessary for the administration of a dose of drug, e.g. 5 minutes. In the shown embodiment the display unit 110 comprises a matrix LCD 114, processor, timer and memory means 112 as well as the system main batteries 115, e.g. 2×CR1225, which is used to charge smaller secondary batteries 105 housed in the measuring unit. The measuring unit comprises 5 3D magnetometers 107 as well as supporting electronic components 102 allowing magnetic data capture and storage thereof until data can be transmitted to the cap unit for further processing via galvanic contacts 106, 116 arranged on the two units, the contacts also allowing charging of the secondary batteries. The measuring unit comprises a mounting ring 108 adapted to engage the standard cap coupling means provided on a FlexTouch® pen, however, in order to secure a safe and secure mounting the coupling components on the mounting ring may be designed to provide a firmer grip than a standard cap.

By designing the sensor ring to be mounted on the pen in a rotating motion, a scenario in which the sensor system is rotated relative to the magnet in a fixed position is present. This could be used to adjust e.g. sensor offset- and gain-values by detecting maximum measurements during mounting of sensor ring on pen. The system could then be calibrated to the actual pen and any look-up table then be adjusted to compensate for any rotational offset in magnet or rod orientation to increase accuracy and reliability.

Figure 13A:
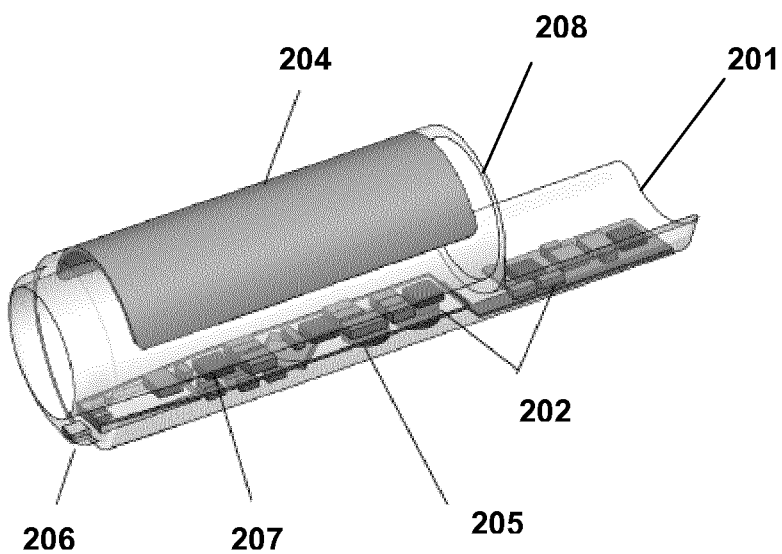
FIGS. 13A-13C show a second embodiment of a measuring system for a drug device.
Figure 13B:
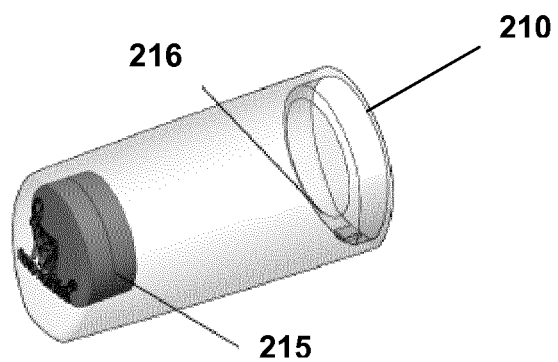
Figure 13C:
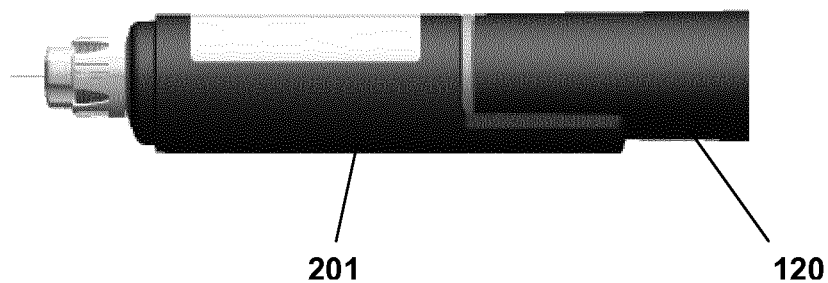

FIGS. 13A-13C show an alternative embodiment of a two-unit measuring assembly. In contrast to the FIG. 9 embodiment all components apart from the main battery 215 is located in a ring-formed measuring unit 201 which then also comprises the display 204 which in the shown embodiment is of the e-ink type. As for the first embodiment, removal and re-attachment of the cap can be used to define a dosing event.

Figure 14A:
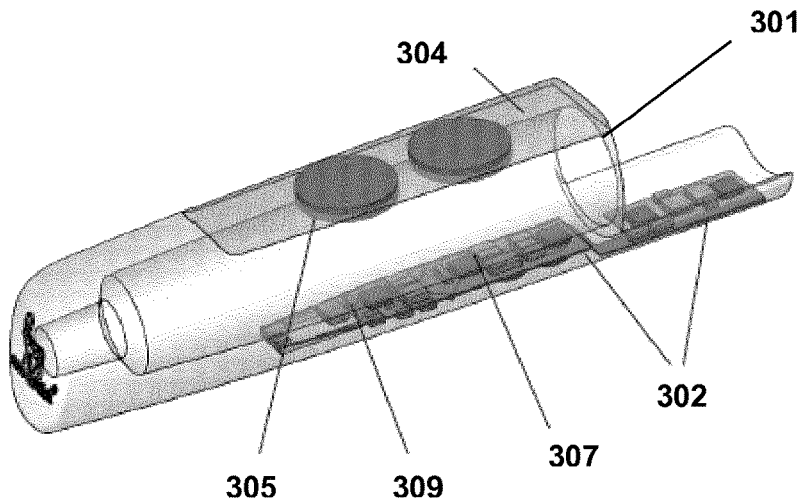
FIGS. 14A and 14B show a third embodiment of a measuring system for a drug device.
Figure 14B:
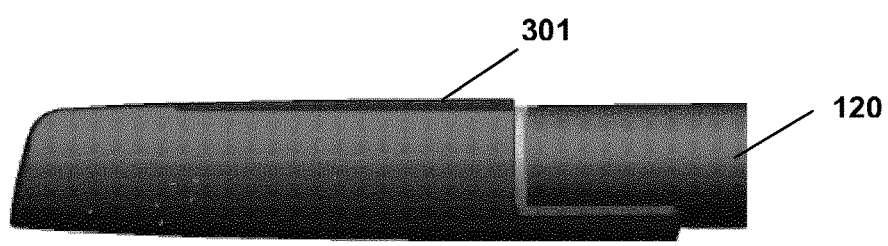

FIGS. 14A and 14B show a further embodiment in which all of the above-described measuring and display components are arranged in a unitary cap unit 301, comprising a display 304, all the electronics 302, and the batteries 305. In addition to the above described components, this embodiment comprises an optical reader 309 adapted to capture information provided for a given drug cartridge.

For all of the above embodiments, communication means may be provided allowing wired or wireless transfer of data, e.g. upload of measured data to a PC or smartphone, or download of new software.

In the above embodiments for a measuring system adapted for use with a pre-filled drug delivery device have been described, however, the same systems could be used in combination with a durable drug delivery device adapted to be re-loaded with a new cartridge when a first has been used, and which comprises e.g. a piston rod rotating during axial displacement. Indeed, for a durable device the components of the measuring system could be fully or partly integrated in the device.

Figure 15:
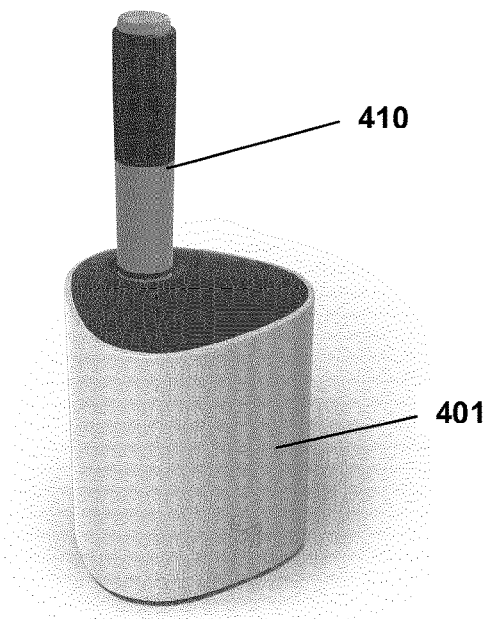
FIG. 15 shows a fourth embodiment of a measuring system for a drug device.

As a further alternative the measuring system could be incorporated in a docking station 401 intended for stationary use with a pen 410 as shown in FIG. 15. Such an arrangement may be relevant for users in need of e.g. a single daily dose of drug, e.g. in the morning or at bedtime, for which purpose the drug delivery device could be placed in the docking station during the day and only be removed there from for a short period of time when the daily dose is to be taken.

As appears from the above, the size of a dose of drug is based on the determination of two piston rod positions, however, this requires that the two positions are determined for the same device and not for two different devices which could be the case, especially if the measuring system is in the form of a unitary cap device which easily by mistake could be reattached to a wrong drug delivery device, or a docking station in which a "wrong" pen may be positioned. To prevent such un-intended pen shifts, the drug delivery device (or cartridge) could be provided with a unique identifier adapted to be recognized by the measuring device, e.g. a 2D matrix code on the cartridge and an optical reader in the cap or docking station. For embodiments comprising a "semi-fixed" measuring and memory unit (e.g. as in FIGS. 13A-13C) each attachment to a drug delivery device could prompt the unit into a "new device" mode. In case the processor and memory is provided in the cap unit (e.g. as in FIGS. 12A-12C) the two units of a given system could be paired and programmed to only work in combination. A more detailed description of means for capturing an identifier is given below with reference to FIGS. 16-18.

In FIGS. 12-15 embodiments are shown utilizing conventional electronics design, however, alternatively printed electronic circuits could be implemented to fully or partly replace conventional circuit technology. Printed electronic is based on standard printing technologies, using different types of ink materials to build electronic circuits and components by printing different patterns in different materials in a number of layers. Inks are made from organic and inorganic materials as well as substrates, depending on purpose. Organic materials are mainly conjugated polymers which possess conducting, semiconducting, electroluminescent, photovoltaic and other properties. Inorganic materials (based on metals such as silver particles, gold particles, aluminium particles, copper doped phosphor) are used for higher order layers and interfaces that organic and polymer materials cannot provide. Substrates such as Polyethylene terephthalate-foil (PET), Polyethylene naphthalate foil (PEN) and Polyimide foil (PI) are used as a carrier to print the electronics on for later transfer to end product. Paper can also be used to some extent.

By printing a number of layers of different patterns and materials, an electronic circuit with conductive leads and components as well as a power source (battery), energy harvesters and display can be created. These materials and processes are now commercially available. Since most of disposable drug delivery devices are made of plastic materials, electronics may be printable directly to the surface of the components with no need of a carrying substrate. When a device is to be fitted with more advanced sensors and functionality as the shown volume detection systems, the display unit and to some extend some of the necessary electronic circuitry can be based on printed electronics. By printing the electronic circuits, sensors, power source, components and display on the injection devices, the added features will have little or no impact on the physical size and design requirements of the injection device, thereby significantly improving marketing ability. Furthermore, printing the electronics will enable significantly reduced production costs compared to traditional electronic circuits, since production can be performed more efficient and material use is greatly reduced.

If the drug delivery device is provided with a spring tensioned during dose setting, e.g. a FlexTouch® pen, an adjusted dose detection system may be realized by measuring the change in magnetic field of the tensioning of the drive spring in the expelling mechanism with the magnetometer nearest the spring.

Further, when using a magnetometer based volume detection system, a small error of measurement may occur if the sensor system determines remaining volume while the user is still actuating the release button of e.g. a FlexTouch® pen. When the release button is actuated, the drive spring moves slightly in the axial direction. By detecting the small change in axial direction of the spring, e.g. of the distal spring "hook" by using the magnetometer sensors, the system can avoid measuring remaining volume in the reservoir while the release button is actuated.

As an alternative to the above-described embodiments a simple volume/dose-detection system could be made using a number of simple one-dimensional magnetometers along the side of a pen reservoir and have a small magnet built-in to the piston rod. The system could determine the position of the piston rod simply by detecting which magnetometer(s) give the most signal. Such a concept would be simple, however, it may be sensitive to disturbing external fields and may require a large number of sensors to meet requirements of accuracy.

Electronic identification systems can be divided into two groups, type identifiers and unique identifiers, where type identifiers are able to only identify the type of device or contents but are not able to distinguish between two identical devices of the same type. The unique identifiers are able to not only identify the type of device and contents but also the unique identity of a device and thus able to distinguish two identical devices from each other.

FIGS. 16A-16E show an embodiment of a measuring unit 601 of the semi-fixed type adapted to be attached to a pre-filled pen-formed drug delivery device 610 for the operational life time of the device, i.e. until the drug reservoir (cartridge) has been emptied. The drug delivery device may be of a type corresponding to e.g. a FlexTouch® or a FlexPen® from Novo Nordisk. The pen is provided with an identifier corresponding to the specific drug content in the reservoir, and the measuring unit as provided with means for capturing this information. More specifically, the pen body is provided with one or more protrusions 611 creating a simple code corresponding to the contained drug, e.g. a long-acting insulin 100 IU/ml, a long-acting insulin 200 IU/ml, a fast-acting insulin 100 IU/ml or a fast-acting insulin 200 IU/ml. The measuring unit is provided with a number of corresponding contacts 603 adapted to be activated by the protrusions when the unit is mounted on the pen body as shown in FIGS. 16A and 16B. FIGS. 16C-16E shows 3 examples of code patterns. The measuring unit may be adapted to detect when a cap (not shown) is taken off and mounted again, this initializing two measurements of the piston position on the basis of which an expelled dose amount can be calculated.

Figure 17:
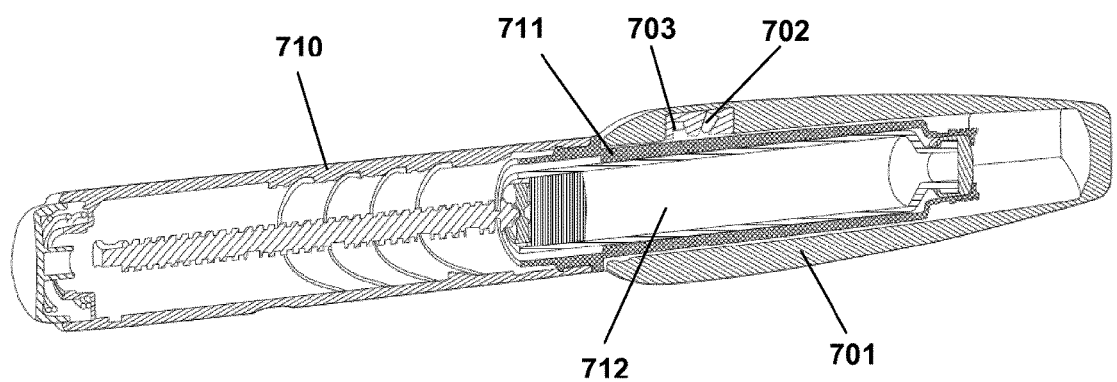
Figure 18A:
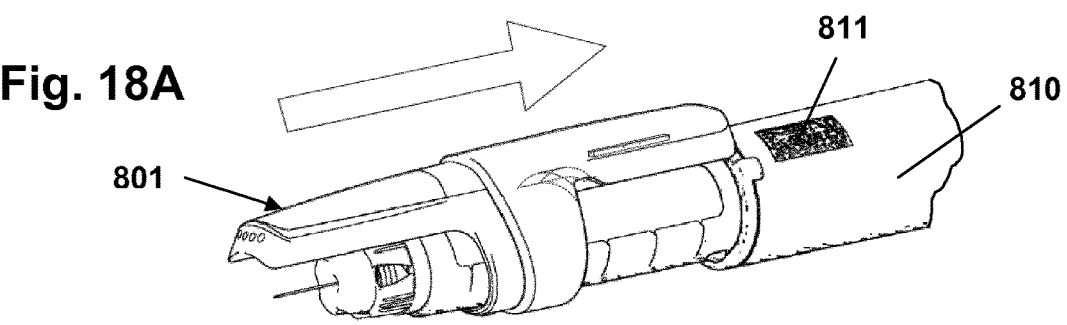
FIGS. 18A-18E show a yet further capture device comprising means for detecting an identifier In the figures like structures are mainly identified by like reference numerals.
Figure 18B:
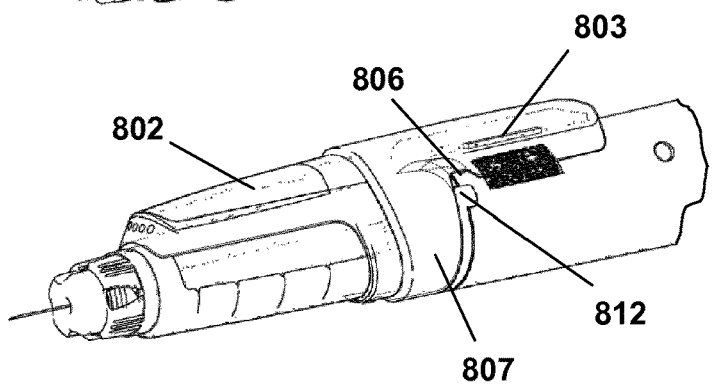
Figure 18C:
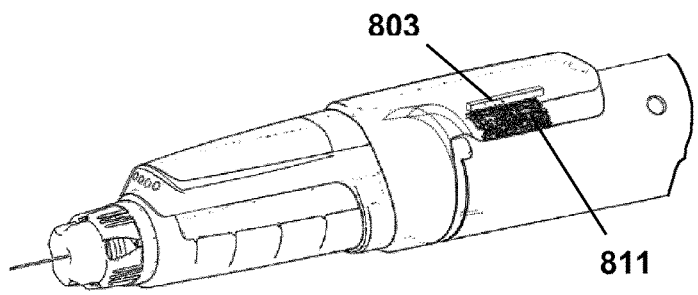
Figure 18D:
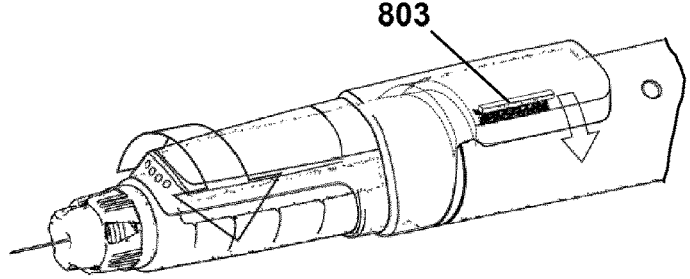
Figure 18E:
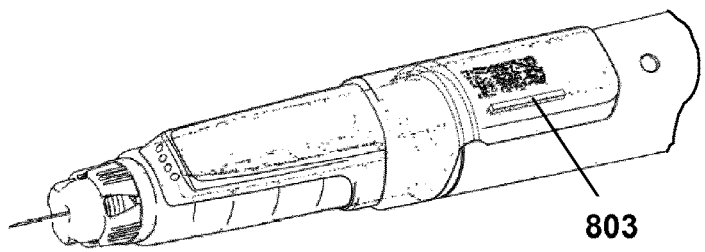

FIG. 17 shows an embodiment of a measuring unit in the form of a cap unit 701 adapted to be attached to a pre-filled pen-formed drug delivery device 710 when the device is not in use. The drug delivery device may be of a type corresponding to e.g. a FlexTouch® or a FlexPen®. As appears, for the internal parts of the device only the drug cartridge 712 and the piston rod are shown. The pen is provided with an identifier in the form of a coloured cartridge holder corresponding to the specific drug content in the reservoir, e.g. orange for a fast-acting insulin 100 IU/ml and green for a long-acting insulin 100 IU/ml, and the measuring unit as provided with means for capturing this information. More specifically, the measuring unit is provided with a white LED 702 is fitted in such a way, that it will enlighten the colour-coded part of the pen, as well as an RGB-sensor chip 703 fitted in such a way, that the area enlightened by the white LED is visible to the RGB-sensor. A shielding to prevent the RGB-sensor to be exposed to direct light from the white LED is arranged between the two. In the figure the remaining electronic components of the cap are not shown. When the light from the white LED containing all colours hits the coloured surface only light with the same colour as the part is reflected to the RGB-sensor, this allowing the RGB composition of the reflected light to be analysed and the colour and thereby type of pen and drug identified. The cap unit may be adapted to detect when the cap unit taken off and mounted again on the pen body, this initializing a measurement of the piston position when the cap is mounted on the basis of which an expelled dose amount can be calculated, i.e. the position for the previous use of the device has been stored. The cap unit may be programmed to work with only one type of pen, i.e. one colour, or with two or more different types of pens. In the latter case the cap unit may be used with only one type of pen at a time, or it may be used with e.g. two types of pens at a time, this being relevant for diabetics using both long-acting and fast-acting insulin. As the colour typically will be detected each time the pen is activated, the pen may automatically detect whether a dose has been expelled or a shift of device has taken place.

FIGS. 18A-18E show an embodiment of a measuring unit 801 of the semi-fixed type adapted to be attached to a pre-filled pen-formed drug delivery device 810 for the operational life time of the device, i.e. until the drug reservoir (cartridge) has been emptied. The drug delivery device may be of a type corresponding to e.g. a FlexTouch® or a FlexPen®. The pen is provided with an identifier in the form of a 2D barcode in printed electronic leads corresponding to the specific drug content in the reservoir, and the measuring unit as provided with a corresponding capacitive fingerprint reader 803 for capturing this information.

There are basically two different scanner technologies available, optical scanners and capacitive scanners. Capacitive scanners are well suited for pen identification since they can be made very small and compact and requires very little power compared to optical scanners. A capacitive fingerprint scanner in principal consists of one or more semiconductor chips containing a line or an array of small cells, each cell including two conductive plates covered by an isolating layer and being smaller than the ridges and valleys of the skin on a finger. Each cell is connected to a small electrical circuit with an inverting operational amplifier, a so called integrator. Prior to scanning the reset switch is closed applying an input reference voltage to both conductor plates which shorts the amplifiers in- and out-puts and "balances" the integrator circuit. When the Reset switch is opened again the processor applies a fixed charge to the integrator circuit. If any capacitive object is placed close the conductive plates (normally the skin of a finger) the capacitance of the system will change and since one of the conductive plates are connected to the inverting terminal, the amplifiers input will change and subsequently the amplifier output will change. By substituting the ridges and valleys of the skin in a fingerprint with a pattern of small conductive leads printed on the pen (or a carrier foil fitted on the pen) the small cells can detect if a printed lead is present below the insulating layer of the conductor plates or not. Due to the size of these small cells a large number of cells can be fitted in a small area and thus large quantities of information can be stored and read on a small area, allowing for long serial-numbers to be identified. Such a serial-"pattern" will be difficult to counterfeit since not only the pattern but also the capacitive properties has to be correct. Next it will be described how such a system could be implemented on a pen with the electronic dose detection unit comprising a capacitive fingerprint line scanner.

A capacitive fingerprint reader 803 is incorporated in an electronic unit 802 for dose detection in such a way, that when the electronic measuring unit is slid onto the pen 810 a tap 812 on the pen ensures that the fingerprint reader is clear of the 2D barcode 811 printed in electronic leads on a foil and placed behind the tap on the pen. When the tap meets the mounting ring 807 of the measuring unit and cannot move any further, the user can start rotate the unit to secure it to the pen. When rotation begins the tap enters a track 806 which guides the unit to perform a rotational movement without sliding along the axis of the pen. During the rotation the fingerprint scanner reads the 2D code on the pen line by line and when the unit is secured to the pen the electronics in the unit will have identified exactly what pen and type the electronic measuring unit is fitted on and be able to give read-outs of actual dose and type instead of just the detected volume of the dose.

Alternatively, a simple optical barcode-reader could be implemented using the mounting of the electronic unit on the pen to perform the sweep and use a simple, low-power LED as light source. However, a barcode based on simple reflection of light from an LED will require relatively wide bars and spacing and thus result in physically long barcodes compared to barcodes based on laser reading. Therefore such a system would mainly be applicable on larger units where one part is mounted on the other with a sufficient long sliding- or rotational movement to cover the necessary number of digits in the barcode.

A unique identification system could also be based on a NFC ID-chip and a build-in chip-reader in the electronic unit. This technology is commonly known and widely used for such purposes, however, for a disposable drug delivery device it may be more expensive than the above-described embodiment based on a fingerprint reader.

When information in respect of a specific type of drug has been identified, this information could also be used to provide a user with further information. By reading the code the unit becomes aware of the drug type and could inform the user of necessary actions say just before an injection or just after an injection. Furthermore, the information of the drug could be stored in the electronic unit and transferred to an external device, e.g. a Personal Computer (PC) or a mobile phone. The external device could then display the information and thus act as a display for the electronic unit which may be provided with only a simple numeric display. The information of the drug could also be stored on a server, and the electronic unit could send the unique code to the external device. The external device would then retrieve the drug specific information from the server using the unique code. This drug-identifying functionality could also be incorporated in an electronic drug delivery device per se not related to a dose detecting unit.

Examples

1. A drug delivery system, comprising:
(a) a drug delivery device 610, 710, 810 comprising:
   a reservoir containing a drug,
   a drug expelling mechanism for expelling drug from the reservoir, and
   an identifier 611, 711, 811 representing information for the specific drug type contained in the reservoir or the specific drug delivery device,
(b) a capture assembly 601, 701, 801 releasably mountable on the drug delivery device, comprising:
   an electronically controlled capturing system for capturing data representing a property related to the amount of drug expelled from the reservoir by the expelling means,
   electronically controlled means 603, 703, 803 for capturing information from the identifier,
   logging means adapted to create a log for amounts of drug expelled from the reservoir based on captured data, wherein the log is created for a given identifier.

2. A drug delivery system as in example 1, wherein the identifier represents a given specific type of drug.
3. A drug delivery system as in example 1, wherein the identifier represents a given unique drug delivery device.
4. A drug delivery system as in any of examples 1-3, wherein the identifier is a colour.
5. A drug delivery system as in any of examples 1-3, wherein the identifier is in the form of a barcode.
6. A drug delivery system as in any of examples 1-3, wherein the identifier is the form of a pattern of conductive elements 811.
7. A drug delivery system as in example 5 or 6, wherein the means for capturing information from the identifier comprises a sensor 803 adapted to capture information during movement of the sensor relative to the identifier.
8. A drug delivery system as in example 22, wherein the drug delivery device and the capture assembly comprises corresponding releasable mounting means adapted to mount the capture device in a pre-defined position relative to the drug delivery device, the mounting requiring a specified translational movement between the drug delivery device and the capture assembly, the translational movement allowing the sensor to capture information from the identifier.
9. A drug delivery system as in any of examples 16-23, wherein the system comprises at least two drug delivery devices, each comprising a unique identifier.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:
1. A system comprising:
   a sensor assembly comprising one or more sensors each measuring position by measuring a magnetic field using a 3D magnetometer corresponding to three axes (X, Y, Z) arranged perpendicularly relative to each other,
   a moveable element moveable relative to the sensor assembly by a combined axial and rotational movement corresponding to a pre-defined axis, the rotational movement having a pre-determined relationship to the axial movement,
   a magnet mounted to the moveable element and moving together therewith, the magnet configured to generate a spatial magnetic field which relative to the sensor assembly varies corresponding to both the axial and rotational movement of the magnet and thus the moveable element, thereby generating a spatial magnetic field which varies uniquely relative to each sensor, and
   a processor configured to determine on the basis of measured values an axial position of the moveable element, wherein,
   the processor, on the basis of the measured values:
      determines an initial axial position of the moveable element using 3D magnetometers,
      determines a rotational position of the moveable element using 3D magnetometers, and
      calculates a corrected axial position of the moveable element, wherein the calculation is based on the determined initial axial position, the determined rotational position, and the pre-determined relationship between the rotational and the axial movement.

2. The system as in claim 1, wherein the sensor assembly is configured spatially as one or more rings each consisting of two or more sensors placed around the pre-defined axis.

3. The system as in claim 1, wherein the magnet is an induced magnet.

4. The system as in claim 1, wherein the moveable element is moved corresponding to a threaded relationship between the moveable element and an additional element.

5. The system as in claim 1, comprising a drug delivery device comprising:
   a reservoir or structure for receiving a reservoir for a drug, the reservoir comprising an axially displaceable piston and an outlet, and
   a drug expelling mechanism for expelling drug from the reservoir and comprising the moveable element in the form of a threaded piston rod which during an expelling action performs the combined axial and rotational movement thereby axially moving the piston of a mounted reservoir.

6. The system as in claim 5, comprising a measuring unit in which the sensor assembly and processor are arranged, and which is configured to receive the drug delivery device in a pre-determined position, the measuring unit being configured to calculate the size of an expelled dose of drug based on two consecutive determinations of the axial position of the piston rod.

7. The system as in claim 6, wherein the measuring unit is in the form of a cap unit structured to calculate the size of an expelled dose of drug based on two consecutive determinations of the axial position of the piston rod when the cap unit is placed in its mounted position on the drug delivery device to cover the outlet of a mounted reservoir.

8. The system as in claim 6, the drug delivery device further comprising:
   an identifier representing information for a specific drug type contained in the reservoir or a specific drug delivery device,
the measuring unit further comprising:
   structure for capturing information from the identifier,
   logging structure structured to create a log for amounts of drug expelled from the reservoir based on calculated doses of drug, the log being created for a given identifier.

9. The system as in claim 8, wherein the identifier is a colour, in the form of a barcode, or in the form of a pattern of conductive elements.

10. The system as in claim 5, comprising a measuring assembly in which the sensor assembly and processor are arranged, the measuring assembly comprising a measuring unit and a cap unit,
   wherein the measuring unit comprises the sensor assembly as well as coupling structure allowing the measuring unit to be mounted on the drug delivery device with the sensor assembly in a pre-determined position relative to the piston rod, and
   wherein the cap unit is configured to be releasably mounted on the drug delivery device or the measuring unit to cover the outlet of a mounted reservoir.

11. The system as in claim 5, comprising a display controlled by the processor to display a calculated dose of drug.

* * * * *